US012698520B2

(12) United States Patent　　(10) Patent No.:　US 12,698,520 B2
Tao et al.　　(45) Date of Patent:　　Aug. 4, 2026

(54) ANTIMICROBIAL SUSCEPTIBILITY TESTING WITH LARGE-VOLUME LIGHT SCATTERING IMAGING AND DEEP LEARNING VIDEO MICROSCOPY

(71) Applicant: Arizona Board of Regents on behalf of Arizona State University, Scottsdale, AZ (US)

(72) Inventors: Nongjian Tao, Fountain Hills, AZ (US); Shaopeng Wang, Chandler, AZ (US); Hui Yu, Tempe, AZ (US); Shelley Haydel, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 170 days.

(21) Appl. No.: 18/494,225

(22) Filed: Oct. 25, 2023

(65) Prior Publication Data

US 2024/0052395 A1　　Feb. 15, 2024

Related U.S. Application Data

(63) Continuation of application No. 16/500,370, filed as application No. PCT/US2018/026223 on Apr. 5, 2018, now Pat. No. 11,834,696.

(Continued)

(51) Int. Cl.
*C12Q 1/18*　　(2006.01)
*G01N 21/51*　　(2006.01)
(Continued)

(52) U.S. Cl.
CPC .............. *C12Q 1/18* (2013.01); *G01N 21/51* (2013.01); *G06T 7/0012* (2013.01); *G16H 10/40* (2018.01);
(Continued)

(58) Field of Classification Search
CPC ........ G06T 2207/10056; G06T 7/0016; G06V 20/69
See application file for complete search history.

(56) References Cited

U.S. PATENT DOCUMENTS 6,043,048 A　*　3/2000　Johnston .................. C12Q 1/18
435/26
6,472,166 B1　*　10/2002　Wardlaw .................. C12Q 1/18
435/32
(Continued)

FOREIGN PATENT DOCUMENTS

WO　　03054824 A2　7/2003
WO　2014127379 A1　8/2014
WO　2018187548 A2　10/2018

OTHER PUBLICATIONS

Altobelli et al. "Integrated Biosensor Assay for Rapid Uropathogen Identification and Phenotypic Antimicrobial Susceptibility Testing" European Eurology Focus, vol. 3, Nos. 2-3, 2017, pp. 293-299.
(Continued)

*Primary Examiner* — Gandhi Thirugnanam
(74) *Attorney, Agent, or Firm* — Withrow & Terranova, PLLC; Vincent K. Gustafson

(57)　　ABSTRACT

A method for deep learning video microscopy-based antimicrobial susceptibility testing of a bacterial strain in a sample by acquiring image sequences of individual bacterial cells of the bacterial strain in a subject sample before, during, and after exposure to each antibiotic at different concentrations. The image sequences are compressed into static images while preserving essential phenotypic features. Data representing the static images are input into a pretrained deep learning (DL) model which generates output data; and antimicrobial susceptibility for the bacterial strain is determined from the output data.

5 Claims, 17 Drawing Sheets

Related U.S. Application Data

(60) Provisional application No. 62/482,099, filed on Apr. 5, 2017.

(51) Int. Cl.

| | |
|---|---|
| *G06T 7/00* | (2017.01) |
| *G16H 10/40* | (2018.01) |
| *G16H 30/40* | (2018.01) |
| *G16H 50/20* | (2018.01) |

(52) U.S. Cl.

CPC ............ *G16H 30/40* (2018.01); *G16H 50/20* (2018.01); *G01N 2201/1296* (2013.01); *G06T 2207/10016* (2013.01); *G06T 2207/10056* (2013.01); *G06T 2207/20081* (2013.01); *G06T 2207/20084* (2013.01); *G06T 2207/30024* (2013.01)

(56) References Cited

U.S. PATENT DOCUMENTS

| | | | | |
|---|---|---|---|---|
| 6,611,765 | B2 * | 8/2003 | Boeufgras | ................ C12Q 1/18 |
| | | | | 702/19 |
| 8,071,319 | B2 * | 12/2011 | Metzger | ............... G01N 33/561 |
| | | | | 435/7.2 |
| 9,582,877 | B2 * | 2/2017 | Fu | ....................... G01N 21/6452 |
| 9,677,109 | B2 * | 6/2017 | Shamsheyeva | .......... G16B 5/00 |
| 9,841,422 | B2 * | 12/2017 | Goldberg | ............... B82Y 20/00 |
| 10,253,355 | B2 * | 4/2019 | Richards | ............. C12Q 1/6841 |
| 10,655,188 | B2 * | 5/2020 | Jarvius | ................... C12Q 1/689 |
| 10,837,044 | B2 * | 11/2020 | Rolain | ..................... C12Q 1/04 |
| 11,155,484 | B2 * | 10/2021 | Jung | ......................... C12M 1/14 |
| | | | | 435/32 |
| 11,834,696 | B2 | 12/2023 | Tao et al. | |
| 2008/0102122 | A1 * | 5/2008 | Mahadevan | ............ A61L 27/14 |
| | | | | 424/618 |
| 2009/0325210 | A1 * | 12/2009 | Weichselbaum | ......... C12Q 1/10 |
| | | | | 356/450 |
| 2011/0097749 | A1 * | 4/2011 | Mamalaki | .............. C07K 16/26 |
| | | | | 530/387.9 |
| 2012/0077206 | A1 * | 3/2012 | Metzger | ................... C12Q 1/04 |
| | | | | 435/7.1 |
| 2013/0129181 | A1 * | 5/2013 | Glensbjerg | ........... G02B 21/125 |
| | | | | 382/133 |
| 2013/0217063 | A1 * | 8/2013 | Metzger | ................... C12Q 1/04 |
| | | | | 702/19 |
| 2014/0278136 | A1 * | 9/2014 | Shamsheyeva | ....... G06T 7/0016 |
| | | | | 702/19 |
| 2017/0045514 | A1 * | 2/2017 | Tao | ................... G01N 33/56911 |
| 2017/0233786 | A1 * | 8/2017 | Jung | ......................... C12M 1/14 |
| | | | | 435/32 |
| 2017/0298408 | A1 * | 10/2017 | Rolain | ..................... C12Q 1/18 |
| 2018/0010084 | A1 * | 1/2018 | Uematsu | ................. C12Q 1/04 |
| 2018/0089828 | A1 * | 3/2018 | Wiles | ..................... C12M 41/46 |
| 2018/0112173 | A1 * | 4/2018 | Wiles | ................... G06V 20/698 |
| 2018/0129864 | A1 * | 5/2018 | Robinson | ............ G02B 21/365 |
| 2018/0285624 | A1 * | 10/2018 | Robinson | ............ G06V 20/698 |
| 2018/0286038 | A1 * | 10/2018 | Jalali | ................... G06V 20/695 |
| 2019/0251330 | A1 * | 8/2019 | Cotte | ...................... G01N 1/30 |
| 2019/0316172 | A1 * | 10/2019 | Ozcan | ................... G06V 20/69 |
| 2021/0065368 | A1 * | 3/2021 | Tao | ....................... G06V 20/695 |
| 2021/0130868 | A1 * | 5/2021 | Tao | ......................... G16H 50/20 |
| 2021/0224978 | A1 * | 7/2021 | Jarvius | ................... G02B 21/34 |
| 2022/0243246 | A1 * | 8/2022 | Wang | ......................... G06T 5/73 |

OTHER PUBLICATIONS

Baltekin et al. "Antibiotic susceptibility testing in less than 30 min using direct single-cell imaging" PNAS, vol. 114, No. 34, 2017, pp. 9170-9175.

Behera et al. "Evaluation of susceptibility testing methods for polymyxin" International Journal of Infectious Diseases, vol. 14, Issue No. 7, 2010, pp. e596-e601.

Bergeron et al. "Preventing Antibiotic Resistance through Rapid Genotypic Identification of Bacteria and of Their Antibiotic Resistance Genes in the Clinical Microbiology Laboratory" Journal of Clinical Microbiology, vol. 36, No. 8, 1998, pp. 2169-2172.

Cadag, E. "Automated learning of protein involvement in pathogenesis using integrated queries" Dissertation, University of Washington, 2009, 191 pages.

Chen et al. "Big Data Deep Learning: Challenges and Perspectives" IEEE Access, vol. 2, 2014, pp. 514-525.

Chen et al. "Deep Learning in Label-free Cell Classification" Scientific Reports, vol. 6, Issue No. 1, Mar. 15, 2016, 16 pages.

Choi et al. "A rapid antimicrobial susceptibility test based on single-cell morphological analysis" Science Translational Medicine, vol. 6, No. 267, 2014, 13 pages.

Choi et al. "Direct, rapid antimicrobial susceptibility test from positive blood cultures based on microscopic imaging analysis" Nature: Scientific Reports, vol. 7, No. 1, 2017, 13 pages.

Dalgaard et al. "Estimation of bacterial growth rates from turbidimetric and viable count data" International Journal of Food Microbiology, vol. 23, 1994, pp. 391-404.

Davenport et al. "New and developing diagnostic technologies for urinary tract infections" Nature Reviews: Urology, vol. 14, No. 5, 2017, pp. 296-310.

Dutka-Malen et al. "Detection of Glycopeptide Resistance Genotypes and Identification to the Species Level of Clinically Relevant Enterococci by PCR" Journal of Clinical Microbiology, vol. 33, No. 1, 1995, pp. 24-27.

Ertl et al. "Rapid Antibiotic Susceptibility Testing via Electrochemical Measurement of Ferricyanide Reduction by *Escherichia coli* and Clostridium sporogenes" Analytical Chemistry, vol. 72, No. 20, 2000, pp. 4957-4964.

Frymier et al. "Three-dimensional tracking of motile bacteria near a solid planar surface" PNAS, vol. 92, No. 13, 1995, pp. 6195-6199.

Hancock, R. "The end of an era?" Nature Reviews Drug Discovery, vol. 6, 2007, p. 28.

Iriya, R. et al., "Rapid Antibiotic Susceptibility Testing Based on Bacterial Motion Patterns with Long Short-Term Memory Neural Networks," IEEE Sensors, vol. 20, No. 9, May 2020, pp. 4940-4950.

Jean et al. "Methods for Dilution Antimicrobial Susceptibility Tests for Bacteria That Grow Aerobically" Clinical Laboratory Standards Institute, Tenth Edition, Jan. 2015, 110 pages.

Jing et al. "Microfluidic Device for Efficient Airborne Bacteria Capture and Enrichment" Analytical Chemistry, vol. 85, No. 10, 2013, pp. 5255-5262.

Jing et al. "Microfluidic Platform for Direct Capture and Analysis of Airborne Mycobacterium tuberculosis" Analytical Chemistry, vol. 86, No. 12, 2014, pp. 5815-5821.

Kim et al. "Real-time integral imaging system for light field microscopy" Optics Express, vol. 22, Issue No. 9, 2014, pp. 10210-10220.

Kinnunen et al. "Monitoring the growth and drug susceptibility of individual bacteria using asynchronous magnetic bead rotation sensors" Biosensors and Bioelectronics, vol. 26, No. 5, 2011, pp. 2751-2755.

Krizhevsky et al. "ImageNet Classification with Deep Convolutional Neural Networks" NIPS'12: Proceedings of the 25th International Conference on Neural Information Processing Systems, vol. 1, 2012, pp. 1097-1105.

Lauga et al. "Swimming in Circles: Motion of Bacteria near Solid Boundaries" Biophysics Journal, vol. 90, No. 2, 2006, pp. 400-412.

Lee et al. "Multistep Synthesis of a Radiolabeled Imaging Probe Using Integrated Microfluidics" Science, vol. 310, No. 5755, 2005, pp. 1793-1796.

Lissandrello et al. "Nanomechanical motion of *Escherichia coli* adhered to asurface" Applied Physics Letters, vol. 105, No. 11, 2014, pp. 113701.

Liu et al. "Rapid Antimicrobial Susceptibility Testing with Electrokinetics Enhanced Biosensors for Diagnosis of Acute Bacterial Infections" Annals of Biomedical Engineering, vol. 42, No. 11, 2014, pp. 2314-2321.

(56) References Cited

OTHER PUBLICATIONS

Longo et al. "Rapid detection of bacterial resistance to antibiotics using AFM cantilevers as nanomechanical sensors" Nature: Nanotechnology, vol. 8, No. 7, 2013, pp. 522-526.

Mann et al. "Antibiotic Susceptibility Testing at a Screen-Printed Carbon Electrode Array" Analytical Chemistry, vol. 80, No. 3, 2008, pp. 843-848.

Neu, H. "The Crisis in Antibiotic Resistance" Science, vol. 257, Aug. 1992, pp. 1064-1073.

Ng et al. "Beyond Short Snippets: Deep Networks for Video Classification" Proceedings of the IEEE Conference on Computer Vision and Pattern Recognition (CVPR), 2015, pp. 4694-4702.

O'Neill, J. "Rapid Diagnostics: Stopping Unnecessary Use of Antibiotics" the Review On Antimicrobial Resistance, Oct. 2015, 39 pages.

O'Neill, J. "Tackling drug-resistant infections globally: final report and recommendations" The Review On Antimicrobial Resistance, May 2016, 84 pages.

Palmer et al. "Understanding, predicting and manipulating the genotypic evolution of antibiotic resistance" Nature Reviews: Genetics, vol. 14, Apr. 2013, pp. 243-248.

Reller et al. "Antimicrobial Susceptibility Testing: A Review of General Principles and Contemporary Practices" Clinical Infectious Diseases, vol. 49, Issue No. 11, Dec. 2009, pp. 1749-1755.

Rossolini et al. "Update on the antibiotic resistance crisis" Science Direct, Current Opinion in Pharmacology, vol. 18, Oct. 2014, pp. 56-60.

Simonyan et al. "Two-Stream Convolutional Networks for Action Recognition in Videos" NIPS'14: Proceedings of the 27th International Conference on Neural Information Processing Systems, vol. 1, 2014, pp. 568-576.

Sinn et al. "Asynchronous Magnetic Bead Rotation Microviscometer for Rapid, Sensitive, and Label-Free Studies of Bacterial Growth and Drug Sensitivity" Analytical Chemistry, vol. 84, No. 12, 2012, pp. 5250-5256.

Sokolov et al. "Physical Properties of Collective Motion in Suspensions of Bacteria" Physical Review Letters, vol. 109, No. 24, 2012, p. 248109.

Syal et al. "Antimicrobial Susceptibility Test with Plasmonic Imaging and Tracking of Single Bacterial Motions on Nanometer Scale" ACS Nano, vol. 10, Issue No. 1, 2016, pp. 845-852.

Tensorflow, "An end-to-end open source machine learning platform" Accessed Aug. 3, 2021, 11 pages, https://www.tensorflow.org/.

Tran et al. "Learning Spatiotemporal Features with 3D Convolutional Networks" IEEE International Conference on Computer Vision, 2015, 9 pages.

Van Valen et al. "Deep Learning Automates the Quantitative Analysis of Individual Cells in Live-Cell Imaging Experiments" PLOS Computational Biology, vol. 12, No. 11, 2016, 24 pages.

Wiegand et al. "Agar and broth dilution methods to determine the minimal inhibitory concentration (MIC) of antimicrobial substances" Nature Protocols, vol. 3, No. 2, 2008, pp. 163-175.

Ying, Shao-Yao "Generation of cDNA Libraries: Methods in Molecular Biology" Humana Press, vol. 221, 2003, 331 pages.

Yu, H et al., "Phenotypic Antimicrobial Susceptibility Testing with Deep Learning Video Microscopy," Analytical Chemistry, vol. 90, No. 10, 2018, pp. 6314-6322.

Non-Final Office Action for U.S. Appl. No. 16/500,370, mailed Nov. 9, 2022, 11 pages.

Final Office Action for U.S. Appl. No. 16/500,370, mailed May 23, 2023, 13 pages.

Advisory Action, Examiner-Initiated Interview Summary, and AFCP 2.0 Decision mailed Jul. 28, 2023, 4 pages.

Notice of Allowance for U.S. Appl. No. 16/500,370, mailed Aug. 28, 2023, 8 pages.

International Search Report and Written Opinion for International Patent Application No. PCT/US2018/026223, mailed Aug. 13, 2018, 16 pages.

* cited by examiner

ANTIMICROBIAL SUSCEPTIBILITY TESTING WITH LARGE-VOLUME LIGHT SCATTERING IMAGING AND DEEP LEARNING VIDEO MICROSCOPY

RELATED APPLICATIONS

This application is a continuation of U.S. patent application Ser. No. 16/500,370 filed on Oct. 2, 2019 and subsequently issuing as U.S. Pat. No. 11,834,696, which is the U.S. national phase under 35 U.S.C. 371 of International Application No. PCT/US2018/026223 filed on Apr. 5, 2018, which claims benefit of U.S. Provisional Patent Application No. 62/482,099 filed on Apr. 5, 2017, wherein the entire contents of the foregoing applications are hereby incorporated by reference herein.

TECHNICAL FIELD

The present invention relates to antibiotic susceptibility testing (AST), and, more particularly, to a rapid AST apparatus and method with deep learning video microscopy.

BACKGROUND

Antimicrobial resistance or emergence of "superbugs" has become a global health epidemic.[1-3] Acceleration of this epidemic in recent years is primarily caused by the widespread overuse and misuse of antibiotics, prompting bacteria to evolve and develop resistance.[4] To address this threat, it is critical to accurately prescribe effective antibiotics for the patient, which necessitates timely antimicrobial susceptibility testing (AST). Current AST technologies, including disk diffusion and broth dilution methods, often take several days to complete.[5-7] Consequently, healthcare providers often face a dilemma: delaying treatment or prescribing potentially ineffective or broad-range empiric therapy while awaiting AST results. A rapid AST technology would help identify antimicrobial susceptibility at the earliest stage of infection, and allow healthcare providers to prescribe narrow-spectrum antibiotic treatment, thus reducing patient mortality and spread of antimicrobial resistance.[8]

Innovative AST technologies have been pursued using either genotypic or phenotypic approaches.[9] The former detects genes responsible for conferring drug resistance,[10-12] which is powerful, but requires prior knowledge of the genes, detects only the potential of antibiotic resistance, and cannot differentiate viable and non-viable bacterial cells. The latter detects if a bacterium can be effectively inhibited or killed by an antibiotic by measuring its phenotypic features using various detection techniques.[13-24] (See also US Patent Application Publication No. 2017/0233786A1, published 2017 Aug. 17, entitled "Novel bioactivity testing structure for single cell tracking using gelling agents") These techniques typically require immobilization of bacteria on a sensor surface, in a gel, or in sophisticated microfluidic channels for imaging and detection. Furthermore, each of them typically measures one phenotypic feature only, limiting its scope in testing infections by different pathogens. Optical microscopy[13, 14] (see also: US Patent Application Publication No. 2017/0233786A1) is especially attractive due to its capability in imaging multiple phenotypic features of discrete single cells, including cell size, morphology, motion, and division. However, defining and quantifying these features with the traditional image processing method is challenging because a cell can grow in size, change in shape, divide over time, rotate, move around in the solution, and move in and out of the microscopic field of view. These challenges are further highlighted when considering that most optical images are 2D representations of 3D bacterial cells that rotate and move in solution.[25]

As summarized above, antibiotic resistance has become a significant public health threat. Given the long time currently required to make a determination, there is a need to develop a faster AST to enable precise antibiotic administration at the earliest possible treatment stage. Thus, a rapid antibiotic susceptibility testing (AST) technology is needed to provide timely identification of resistant infections and delivery of accurate antibiotic treatment.

The present invention discloses a new and novel rapid AST technology that images single, non-immobilized bacterial cells and analyzes multiple phenotypic features and responses of the cells automatically with a deep learning (DL) algorithm.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

Disclosed herein is a method for deep learning video microscopy-based antimicrobial susceptibility testing of a bacterial strain in a patient sample by acquiring optical image sequences of individual bacterial cells of the bacterial strain in the subject sample before, during, and after exposure to each antibiotic at different concentrations. The image sequences are compressed into static images while preserving essential phenotypic features. Data representing the static images is input into a pre-trained deep learning (DL) model which generates output data; and antimicrobial susceptibility for the bacterial strain is determined from the output data.

BRIEF DESCRIPTION OF THE DRAWINGS

While the novel features of certain embodiments of the invention are set forth with particularity in the appended claims, the invention, both as to organization and content, will be better understood and appreciated, along with other objects and features thereof, from the following detailed description taken in conjunction with the drawings, in which:

DETAILED DESCRIPTION

Figure 1:
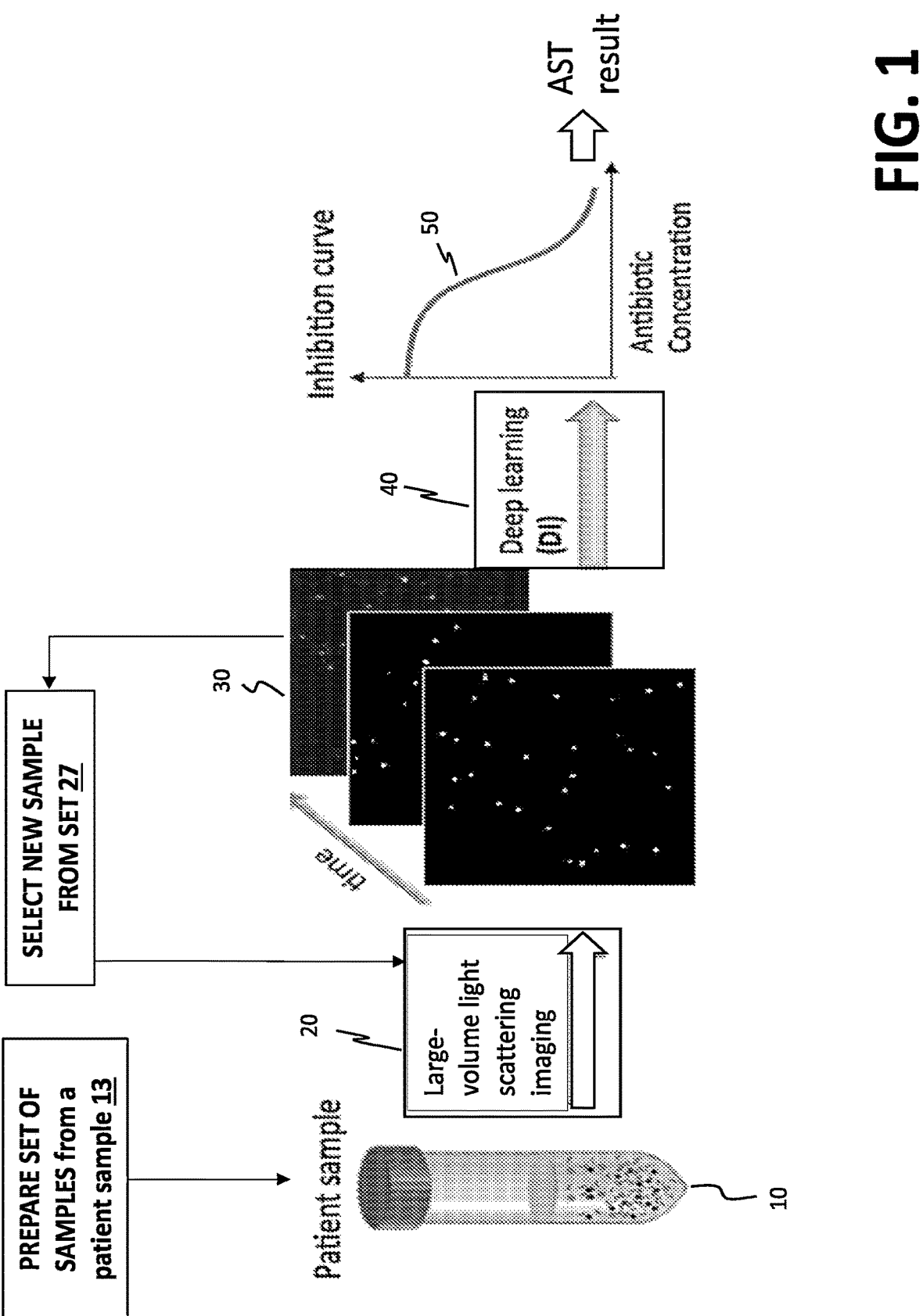
FIG. 1 shows an example of a method for antibiotic susceptibility testing that features a large-volume light scattering imaging (LLSi) technique.

The following disclosure describes a device for antibiotic susceptibility testing (AST). Several features of methods and systems in accordance with example embodiments are set forth and described in the figures. It will be appreciated that methods and systems in accordance with other example embodiments can include additional procedures or features different than those shown in the figures. Example embodiments are described herein with respect to a rapid AST apparatus and method based on a large-volume light scattering imaging technique and a deep learning video micros-copy technique that enables detection of individual bacterial cells in clinical samples. However, it will be understood that these examples are for the purpose of illustrating the prin-ciples, and that the invention is not so limited.

Unless the context requires otherwise, throughout the specification and claims which follow, the word "comprise" and variations thereof, such as, "comprises" and "compris-ing" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or charac-teristic described in connection with the embodiment is included in at least one embodiment of the present disclo-sure. Thus, the appearances of the phrases "in one embodi-ment" or "in an embodiment" in various places throughout this specification are not necessarily all referring to the same embodiment. Furthermore, the particular features, struc-tures, or characteristics may be combined in any suitable manner in one or more embodiments.

Definitions

Generally, as used herein, the following terms have the following meanings when used within the context of microarray technology:

The articles "a" or "an" and the phrase "at least one" as used herein refers to one or more.

As used herein, "AST" means antibiotic susceptibility testing of cells.

"Deep Learning" or "DL," as used herein, is used in its generally accepted meaning as a class of machine learning algorithms using a cascade of many layers of nonlinear processing units, as for example neural networks and adap-tive processors, that can be based on unsupervised or super-vised learning, pattern analysis applications and the like.

"Minimal Inhibitory Concentration (MIC)" is used in its generally accepted meaning as the lowest drug concentration that prevents visible microorganism growth.

"Minimum Bactericidal Concentration (MBC)" is used in its generally accepted meaning as the lowest concentration of an antibacterial agent required to kill a particular bacte-rium.

As used herein, "plurality" is understood to mean more than one. For example, a plurality refers to at least two, three, four, five, ten, 25, 50, 75, 100, 1,000, 10,000 or more.

As used in this specification, the terms "processor" and "computer processor" encompass a personal computer, a tablet computer, a smart phone, a microcontroller, a micro-processor, a field programmable object array (FPOA), a digital signal processor (DSP), an application-specific inte-grated circuit (ASIC), a field programmable gate array (FPGA), a programmable logic array (PLA), or any other digital processing engine, device or equivalent capable of executing software code including related memory devices, transmission devices, pointing devices, input/output devices, displays and equivalents.

"Obtaining" is understood herein as manufacturing, pur-chasing, or otherwise coming into possession of.

"TensorFlow™" is an open source software library for numerical computation using data flow graphs.

In a valuable addition to the art, the present invention provides, for the first time, two key innovations including: 1. A process using large volume scattering imaging (LLSi) an approach that removes the need for (normally culture based and time consuming) bacteria enrichment to enable rapid AST. This approach is non-obvious because using LLSi reduces the optical zoom causing loss of direct morphological information of the bacteria. Instead, in a key innovation that leads to determination of the antibiotic effect on the bacteria, the intensity and motion of the bacteria spots in the images are analyzed to obtain size and shape information of the bacteria. 2. Further, to effectively analyze the large amount of image sequences obtained, each image sequence as compressed into a single stack image, greatly reducing the data amount, but preserving the essential information needed to quantify bacteria phenotypic features (number, size and shape) and thus the antibiotic effect on the bacteria.

As described in the specification and claims herein, this disclosure presents an AST technology that images single, non-immobilized bacterial cells and analyzes multiple phenotypic features and responses of the cells automatically with a deep learning algorithm. DL is an exciting new area of artificial intelligence using large neural networks, and has been used for cell segmentation and classification based on static images,[26, 27] but applying it to AST with live videos of bacteria as input data is non-trivial, and has not been previously been demonstrated until developed for the first time by the inventors herein. Because analysis of the large data volume of the videos are computationally expensive and time consuming, it is non-obvious to analyze large volumes of videos rapidly as is evident by the absence of such techniques in known processes.

In contrast to known technologies, the examples shown here maximize the speed and accuracy of AST by learning multiple phenotypic features at the pixel level without having to define and then quantify each of them. Its self-learning capability allows improvement of AST accuracy over time as the number of analyzed samples increases. To demonstrate DL video microscopy-enabled AST (DLVM-AST) and large volume light scattering imaging (LLSi), *Escherichia coli* (*E. coli*) was selected as a candidate for exploration. *E. coli* is a bacterial pathogen that is the most common cause of urinary tract infections (UTI), and five relevant antibiotics for treating UTI: polymyxin B (PMB), streptomycin, ciprofloxacin, aztreonam, ampicillin, penicillin and combinations thereof. These antibiotics kill or inhibit *E. coli* via different mechanisms, resulting in different cell phenotypic changes, such as motion, morphology and division changes. The capability of LLSi and DLVM-AST was evaluated for automatically identifying and analyzing antibiotic-mediated inhibition of bacterial cells using *E. coli* as an example and determining the minimum inhibitory concentrations (MIC). Results were also compared to results obtained by the traditional imaging processing algorithm13, 14 and the gold standard broth macrodilution (BMD) method.

Referring now to FIG. 1, an example of a method for antibiotic susceptibility testing that features a large-volume light scattering imaging (LLSi) technique is shown. A set of one or more samples are prepared in one or more vials 13 from a patient sample. In each vial a different dose of a selected drug, for example an antibiotic or other medicine used to treat disease and/or inhibit bacterial growth, is added. At least one negative control having no antibiotics added is included in the set of samples. To start the test, a sample 10, selected from the set of samples, is subjected to large volume light scattering imaging 30. The video 30 is processed in a deep learning (DL) algorithm 40 from which an output data point on an inhibition curve 50 is derived. If more than one sample is used, the test is then repeated using a new sample having a different concentration of the selected antibiotic from the set of samples at process step 27. This test process sequence may be repeated for the selected antibiotic until some or all of the patient samples are used.

At this point, if more than one sample is tested, an inhibition curve may be derived. The process may then be repeated for different antibiotics until an AST result or inhibition curves for all selected antibiotics are obtained. Finally, MIC values for all antibiotics are determined from the corresponding inhibition curves. In some examples, it is not necessary to derive an inhibition curve, in those cases, a single point AST result is all that is needed. See, for example, the example described with reference to FIG. 3 hereinbelow.

Following the process described above, the test method measures multiple doses of the selected antibiotic to generate a MIC value for each selected antibiotic. Multiple antibiotics are tested at various doses to finish a complete AST test. Also, although individual bacteria are measured, for the different doses of antibiotics, different individual bacteria were measured. To generate the dose curve, many bacteria are analyzed. Therefore, a sub population of bacteria that are resistant to a drug may be identified. This will be described in more detail with respect to the examples below.

In contrast to previously known methods, LLSi-DL does not require time-consuming culturing and sample enrichment steps, is sensitive to tracking single bacterial cells, and can detect any of the phenotypic features or a combination of different phenotypic features that are most susceptible to antibiotics. These unique capabilities lead to a fast AST technology for UTIs and other antibiotic-resistant strains. The disclosed LLSi-DL consists of two basic components: LLSi to allow detection of individual bacterial cells in a dilute real sample without culturing and enrichment, and DL to quickly determine antibiotic resistance after training.

Figure 2:
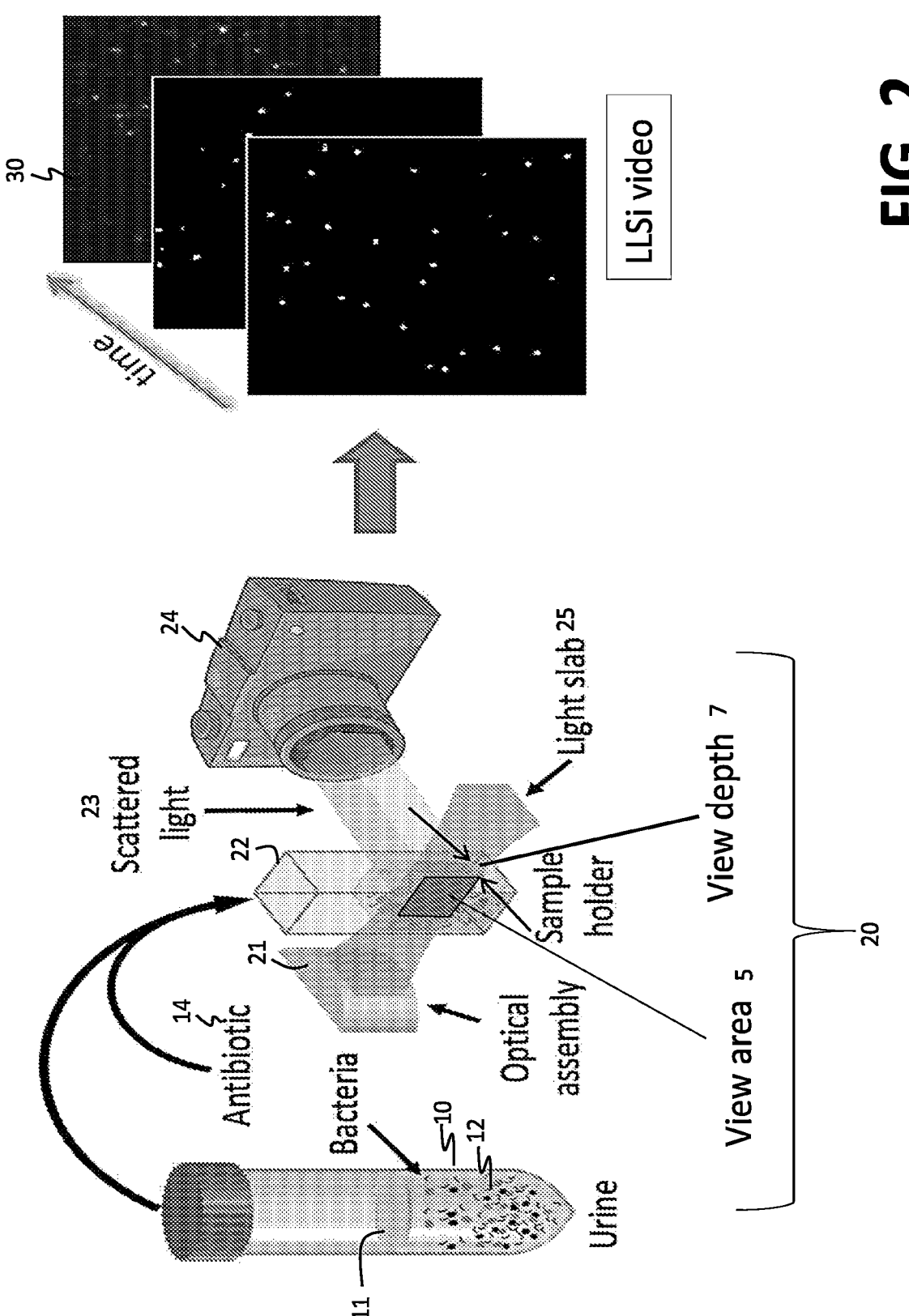
FIG. 2 shows an example of a method for large-volume light scattering imaging (LLSi) consisting of a light source and optics to produce a light slab to illuminate a large volume of the sample, and a large-volume and deep focal depth imaging system to collect scattered light and form a low noise and low background video of the individual bacterial cells at clinically relevant concentrations.

Referring now to FIG. 2, an example of a method for large-volume light scattering imaging (LLSi) consisting of a light source and optics to produce a light slab to illuminate a large volume of the sample, and a large-volume and deep focal depth imaging system having a wide view to collect scattered light and form a low noise and low background video of the individual bacterial cells at clinically relevant concentrations ($10^3$-$10^9$ CFU/mL) is shown. A sample solution 10 includes urine 11 and bacterial cells 12. A large-volume light scattering imaging system 20 includes an optical assembly 21, a sample holder 22 and a camera 24. The optical assembly 21 may include a light source or may transmit light from an external source. The sample holder 22 when illuminated by light slab 25 creates a view area 5 and a view depth 7. The optical assembly and camera may be readily understood by one skilled in the art having the benefit of this disclosure.

The concentration of harmful bacteria in a patient sample can be as low as $10^3$ CFU/mL. Thus, detecting the individual bacterial cells without culturing and sample enrichment is challenging. Optical and AFM techniques can image single bacterial cells, but in certain embodiments sufficient surface coverage of the cells must be ensured because the viewing areas of the high-resolution imaging techniques are small. This makes it challenging to image single bacterial cells in low concentration samples without enrichment via antibody or other trapping methods. For example, with a typical 40× objective with numerical aperture (NA) of 0.65, the depth of field is ~1 μm, and the image area is ~300×300 μm² for ½ inch imager, which gives an image volume of only $3\times10^4$ μm3, or $3\times10^{-8}$ mL. A bacteria concertation of at least $10^8$ cfu/mL in the sample is needed to have at least 1 bacteria to be imaged. Therefore, sample enrichment is a necessary time consuming step for existing microscopy based methods that making rapid antibiotic susceptibility testing (AST) a challenge.

To meet this challenge, disclosed herein is a large-volume light scattering imaging (LLSi) apparatus and method that images single bacterial cells at concentrations as low as $10^3$ CFU/mL without culturing or sample enrichment.

Still referring to FIG. 2, the LLSi apparatus 20 creates a light slab 25 to illuminate a large volume of the sample solution 10 (e.g., bacteria in urine) in the sample holder 2, and image the individual bacterial cells 12 within the volume with the large-volume optical imaging system. Scattered light 23 from the sample holder is transmitted to the camera 24. Images from the camera 24 are used to create a large-volume light scattering imaging video 30 over a period of time.

For practical concentration of $10^3$-$10^9$ CFU/mL, and more preferably, $10^3$-$10^5$ CFU/mL, the view volume must be sufficiently large such that at least 1 bacterial cell will be present. In one advantageous example the view volume (the volume of sample solution that can form an image on the imager) must be at least 1 micro liter (or 1 mm$^3$). In one useful example, the view area 5 must have a value substantially larger than view depth 7. For example, the view area may be in the range of 1-100 mm$^2$ and the view depth in a range between 0.1 mm to 2 mm. Expressed as a ratio, the view area value may be about 10 times larger than the view depth value.

In one example, a viewing area of 7.2 mm×4.8 mm with a focal depth of 1 mm leads to an imaging volume of ~35 mm$^3$, which contains ~35 bacterial cells for a $10^3$ CFU/mL sample. Light scattering imaging allows low noise and low background detection of single bacterial cells within the illuminated volume. However, because large volume imaging requires low optical zoom, LLSi cannot resolve the shape and size of each cell, but it provides the information from the scattered intensity, and its fluctuation over time. It also tracks the metabolically driven motion of each cell. Although the information are less obvious, they can be extracted through the deep learning algorithm described below.

Figure 3:
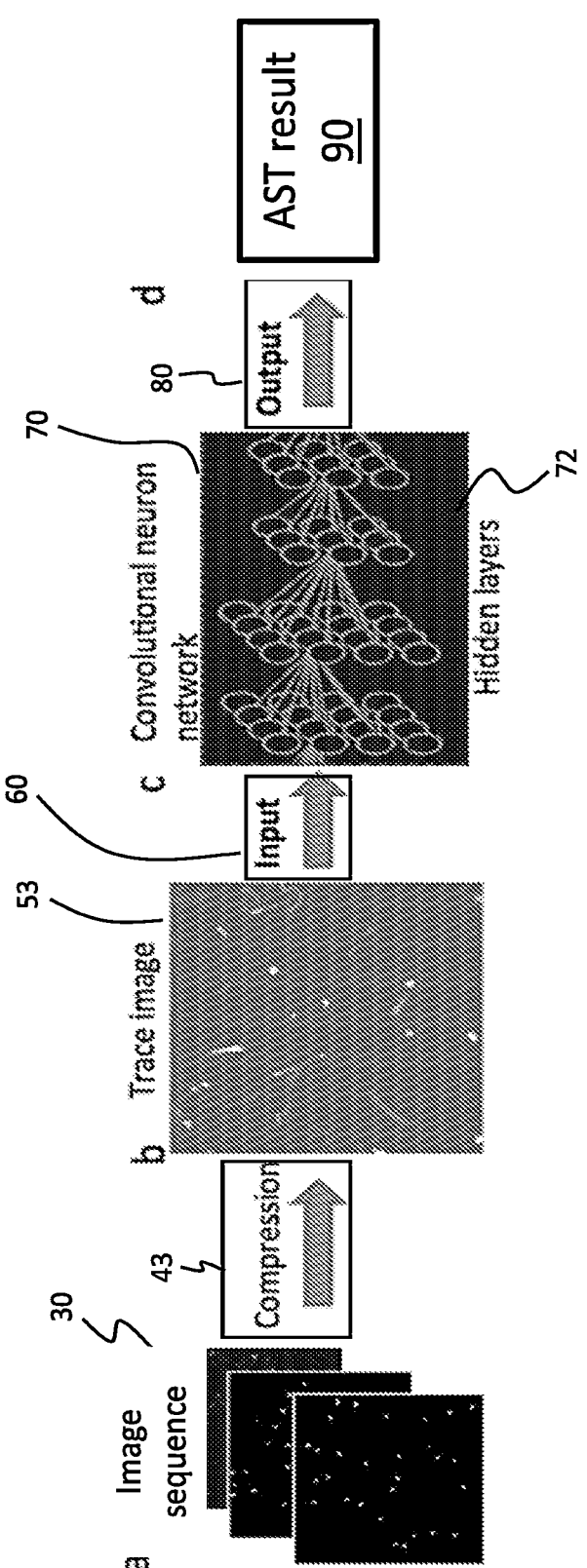
FIG. 3 shows an example of a method for a Deep Learning (DL) algorithm that compresses a video (or an image sequence) into a trace image and feeds it into a convolutional neural network as an input, which is processed by the multiple hidden layers in the neural network to provide an output.

Referring now to FIG. 3, an example of a method for a Deep Learning (DL) algorithm that compresses a LLSi video into a trace image and provide it as an input into a convolutional neural network, which is processed by the multiple hidden layers in neural network to provide an output is shown. An inhibition curve and minimum inhibitory concentration (MIC) may be derived from the output.

The deep learning algorithm disclosed herein provides a solution for detecting antibiotic action on bacteria that leads to changes in various phenotypic features, such as division (growth), metabolic driven motion, and morphology. The gold standard broth microdilution (so as the light scattering intensity based method) detects the optical density, which cannot resolve single bacterial cells, and is limited to growth only. High spatial resolution microscopy can in principle detect multiple phenotypic features, but its viewing area is small (as discussed above) and extracting each of the phenotypic features with the traditional imaging processing and machine learning algorithms is time consuming and often problematic. For example, a bacterial strain exhibits different phenotypic features in response to different antibiotics, and different strains also exhibit different phenotypic features in about response to the same antibiotics. At the single cell level, different bacterial cells of the same strain are also different because of the heterogeneity. Quantifying these features for AST with the traditional imaging processing approach is challenging, especially in cases where an antibiotic leads to changes of multiple phenotypic features.

The deep learning method and apparatus detects antibiotic action on bacteria without specifically identifying and tracking a phenotypic feature. It learns how to differentiate antibiotic susceptible bacterial cells from antibiotic resistant cells automatically by detecting differences in the LLSi videos of individual bacterial cells. The differences include cell division, and morphology change, but also motion associated with metabolic activities, or any of other changes in the LLSi images. DL could also include biochemical features, such as ATP and redox markers, as additional phenotypic features to further improve its specificity and sensitivity. This DL approach provides a universal platform for automatically identifying and analyzing antibiotic susceptibility/resistance for different bacterial strains and antibiotics.

Still referring to FIG. 3, one example of a DL algorithm includes an input 60, a neural network 70 and an output 80, the output being directly proportional to or equaling an AST result 90. Unlike traditional image processing and analysis algorithms, the input in DL is whole LLSi images 30 instead of manually identified and extracted features, such as the number and size of the objects (bacterial cells). The neural network 70 includes multiple hidden layers 72. The multiple hidden layers operate to process features from the input with different levels of details.

In certain embodiments, to learn these features, the neural network 70 must be trained first with a large number of examples. During training, the model automatically learns the features in the examples and store them in the hidden layers. DL has been used in the segmentation and identification of mammalian cells 26.

A frequently encountered difficulty in DL is that the input data are too large to be quickly processed with even a fast computer. This is especially the case when one uses optical videos (e.g., LLSi videos) as an input. In order to overcome this difficulty, prior to processing in the neural network, the LLSi video 30 is processed in compression algorithm 43 into a static trace image 53. Compression algorithm 43 transforms each bacterial cell in the video into a trace. The compression algorithm 43 operates to reflect cell motion and morphology change in intensity and its variation along the trace, and cell division is detected as splitting of a spot into two spots (traces). This reduction of input data size dramatically shortens the training time while it preserves the key information and provides efficient detection on antibiotic action on bacteria.

EXAMPLES

Figure 4A:
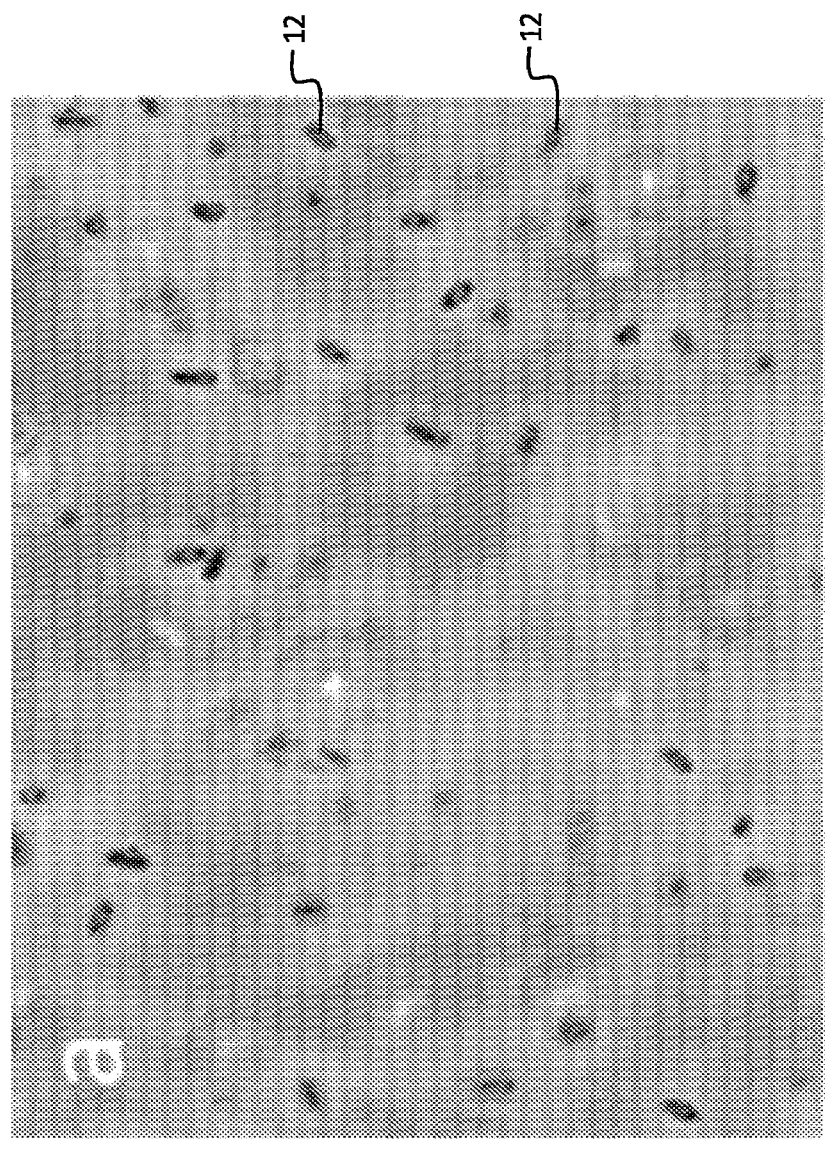
FIG. 4A shows individual *E. coli* cells and their motions revealed by a conventional 40× optical microscope.

Referring now to FIG. 4A, individual *E. coli* cells and their motions revealed by a conventional 40× optical microscope are shown. The inventors here have tested the susceptibility of *E. coli* O157 model strain to Polymyxin B (PMB, an antibiotic) using a 40× optical microscope. The individual bacterial cells 12 were identified, and their motions and growth were tracked using an imaging-processing algorithm. Inhibition curves were derived from the tracking data as shown below with respect to FIG. 4B and FIG. 4C. The MIC value was found to be MIC=2 µg/ml @30 mins, which agrees with that the traditional optical density method. However, the experiment used concentrated bacterial samples, because the microscope has a small viewing size.

Figures 4B, 4C:
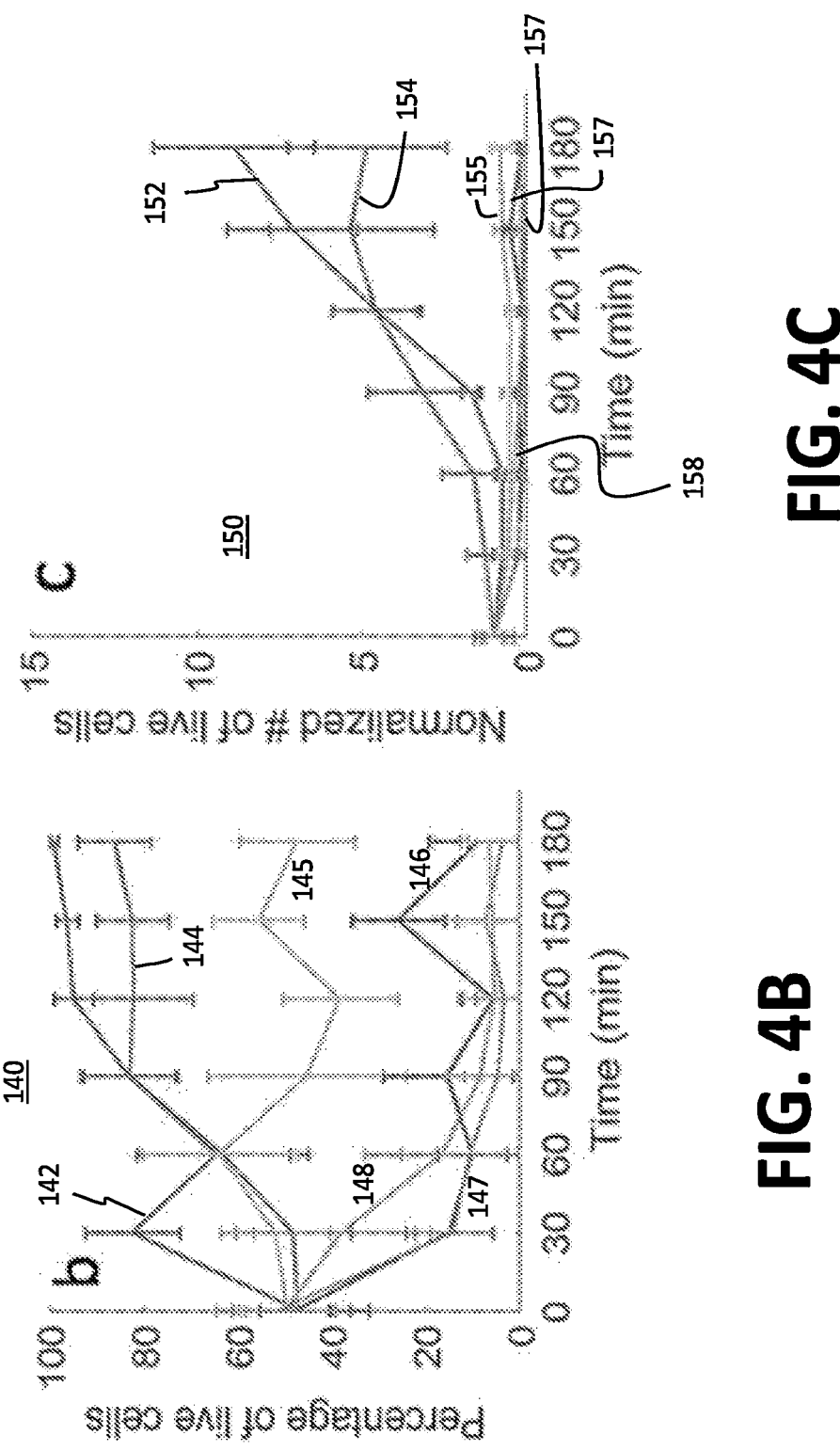
FIG. 4B shows an example of an inhibition curve plotted as the percentage of live cells that PMB has a negative effect on vs. time.
FIG. 4C shows an example of an inhibition curve plotted as the normalized number of live cells that PMB has a negative effect on vs. time.

Referring now to FIG. 4B, an example of an inhibition curve plotted as the percentage of live cell bacteria that PMB has a negative effect on vs. time is shown. The plot 140 shows time in minutes along the X-axis and percentage of live cells on the Y-axis. Curve 142 plots control, curve 144 plots an MIC value of 0.5 µg/ml, curves 145, 146, 147 and 148 plot MIC values of 1, 2, 4 and 8 µg/ml respectively.

Referring now to FIG. 4C, an example of an inhibition curve plotted as the normalized number of live so bacteria that PMB has a negative effect on vs. time is shown. The plot 150 shows time in minutes along the X-axis and the normalized number of live cells on the Y-axis. Curve 152 plots control, curve 154 plots an MIC value of 0.5 µg/ml, curves 155, 156, 157 and 158 plot MIC values of 1, 2, 4 and 8 µg/ml respectively.

Figure 5B:
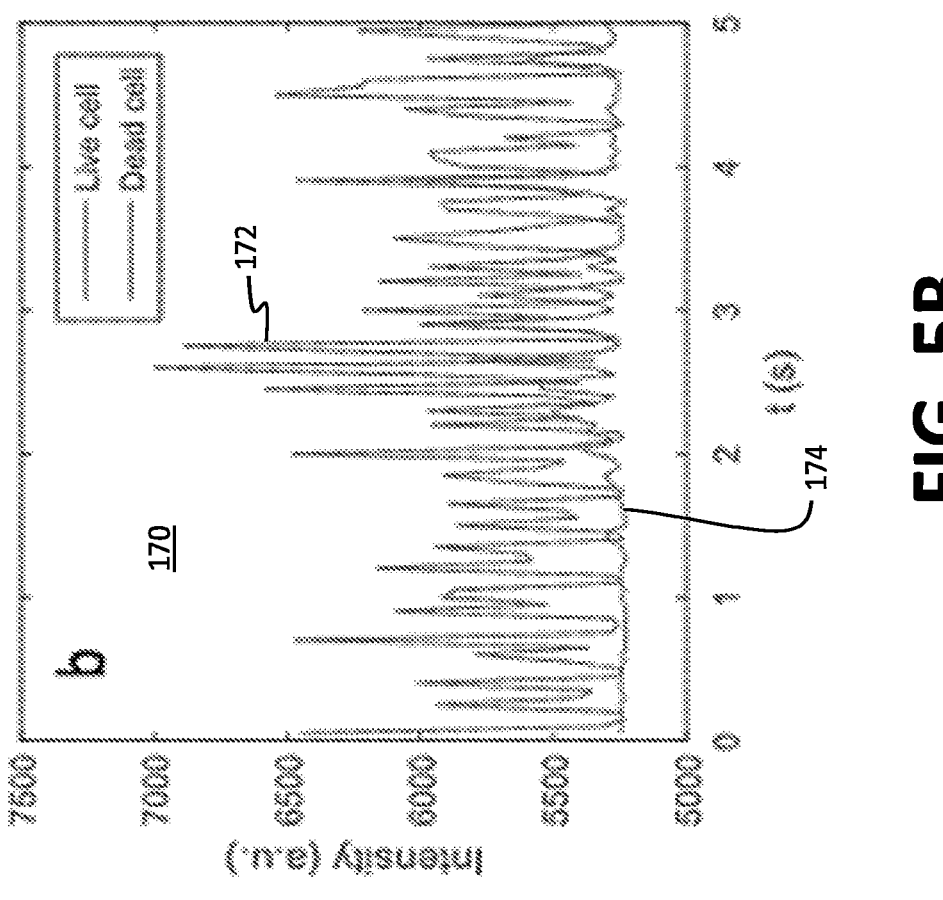
FIG. 5B shows an example of intensity changes over time for a live and a dead bacterial cell, showing large intensity fluctuations in the live cell.
Figure 5A:
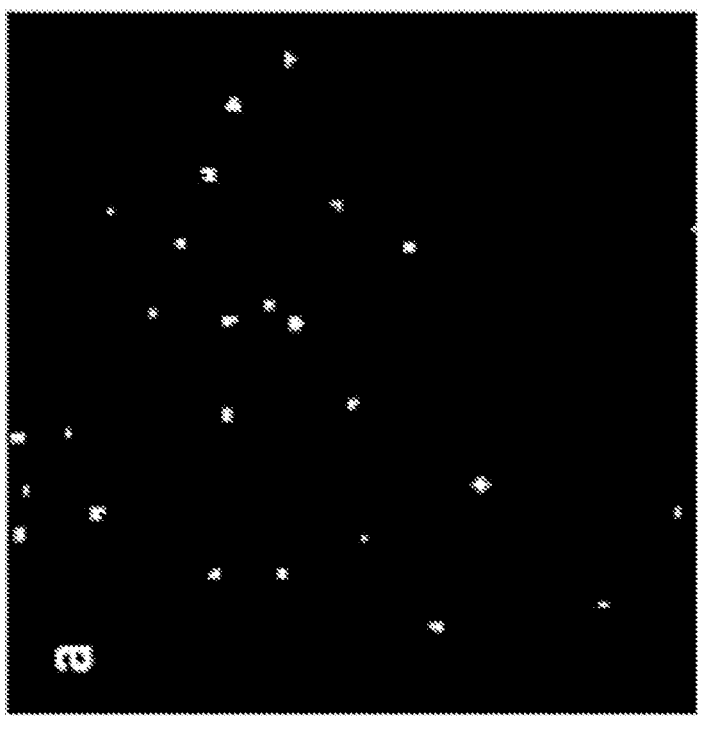
FIG. 5A shows an example of an LLSi image of *E. coli* ($10^3$ CFU/mL) in a urine sample, where the individual bacterial cells are shown as bright spots.

Referring now to FIG. 5A, an example of an LLSi image of *E. coli* ($10^3$ CFU/mL) in a urine sample, where the individual bacterial cells are shown as bright spots is shown. A prototype LLSi, was used to image single bacterial cells (*E. coli* O157: H7) spiked in real urine with concentrations as low as $10^3$ CFU/mL. The resultant LLSi video reveals each bacterial cell as a bright spot 160. The bright spots 160 allowed tracking of bacterial growth (division), and motion. Additionally, large intensity fluctuations (as shown in FIG. 5B) due to the rotation of the *E. coli* were observed. Note that the intensity fluctuations of live cells are much greater than those of dead cells, indicating that the intensity is a useful phenotypic feature for AST.

Referring now to FIG. 5B, an example of intensity changes over time for a live bacterial cell and a dead bacterial cell, showing large intensity fluctuations in the live cell is shown. Plot 170 shows time in seconds on the X-axis and intensity units on the Y-axis. Live cells are plotted on curve 172 and dead cells are plotted on curve 174.

Determining Antibiotic Action and MIC of *E. coli* with DL

Figure 6A:
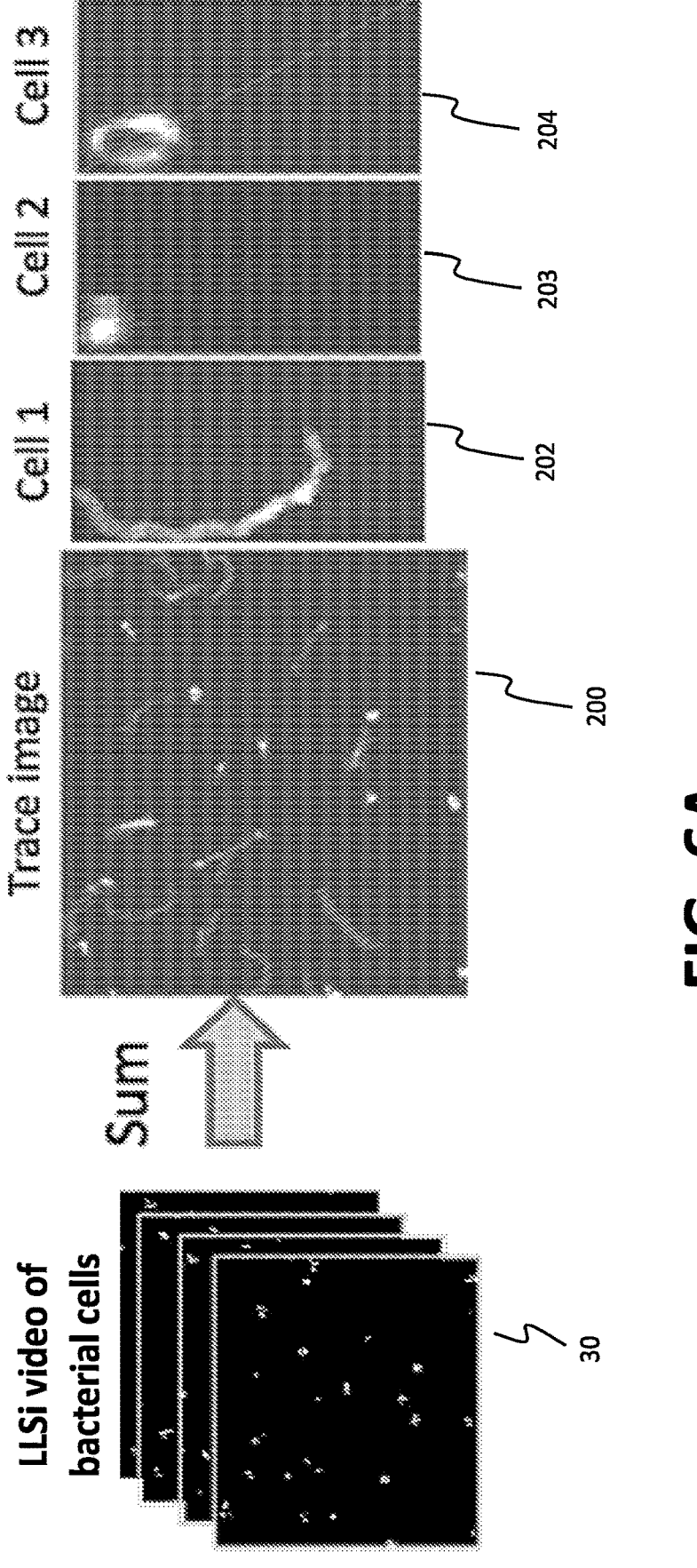
FIG. 6A shows an example of an LLSi video frame showing individual bacterial cells as bright spots moving in sample solution.
Figure 6C:
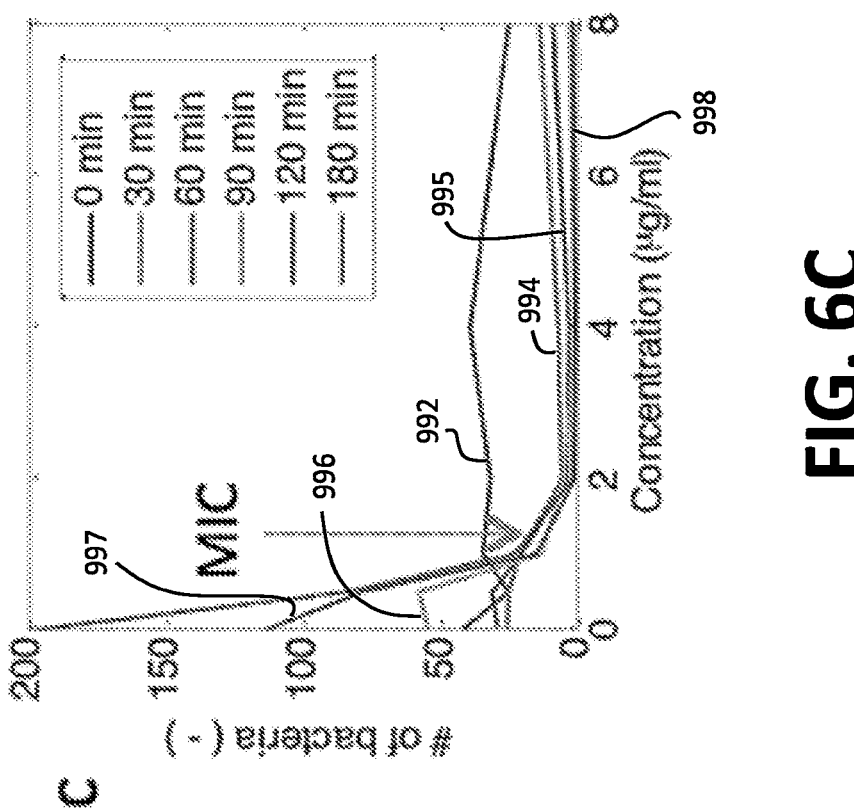
FIG. 6C shows an example of an inhibition curve where the curve shows the number of bacterial cells vs. antibiotic concentrations at different times.
Figure 6B:
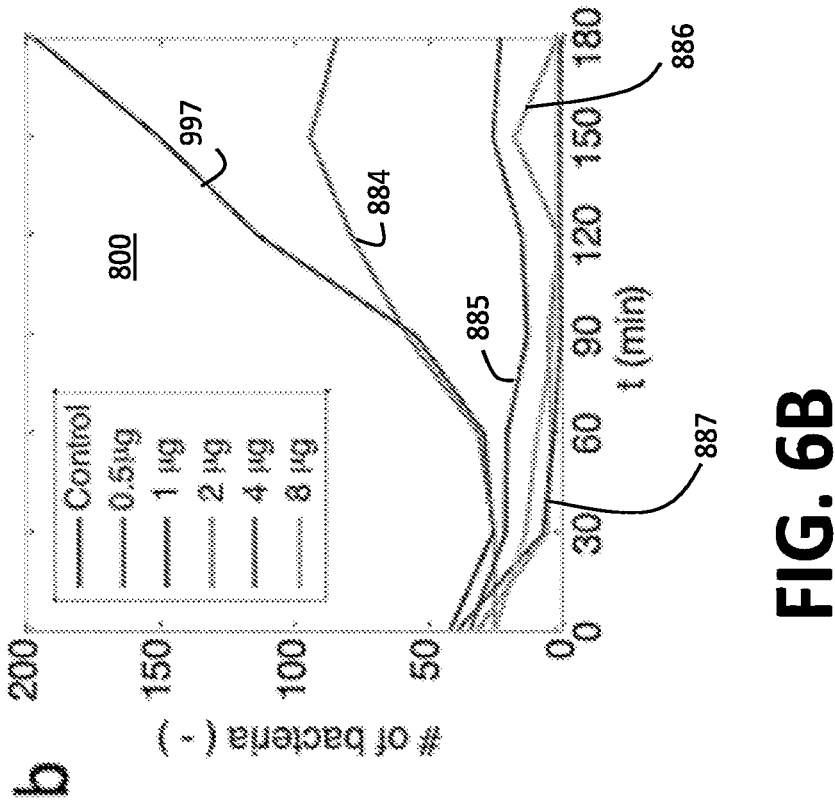
FIG. 6B shows an example of an inhibition curve where the number of bacterial cells vs. time at various antibiotic concentrations.

Referring now to FIG. 6A an example of an LLSi video frame showing individual bacterial cells as bright spots moving in sample solution is shown. DL was applied to study antibiotic susceptibility of *E. coli* O157: H7. A LLSi video 30 was first recorded and preprocessed to remove background. The background corrected video was then compressed into a static trace image 200, which was used as the input of the DL model. Panels 202, 203 and 204 are magnified images of individual cells, namely, cell 1, cell 2 and cell 3 from the trace image 200. The DL model included two hidden convolution layers and two hidden subsampling layers to model the image features, and a fully connected output layer to classify the features. The output of the DL model is either a definite antibiotic effect or no antibiotic effect on each of the bacterial cells at a given antibiotic and concentration, from which an antibiotic inhibition curve was plotted to show the number of bacterial cells with no antibiotic effect at the concentration (FIGS. 6B and 6C). From the antibiotic inhibition curves, the MIC value was determined, which agrees with that from the gold standard test. Note that the MIC in the DL method was determined from the video without extracting a specific feature, which is different from the traditional imaging processing approaches.

Referring now to FIG. 6B, an example of an inhibition curve where the number of bacterial cells vs. time at various antibiotic concentrations is shown. Plot 800 shows the number of bacteria (–) on the Y-axis and time in minutes on the X-axis. Curve 882 plots control, curve 884 plots an MIC value of 0.5 µg/ml, curves 885, 886, 887 and 888 plot MIC values of 1, 2, 4 and 8 µg/ml respectively.

Referring now to FIG. 6C, an example of an inhibition curve where the curve shows the number of bacterial cells vs. antibiotic concentrations at different times is shown. Plot 900 shows the number of bacteria (–) on the Y-axis concentration in µg/ml on the X-axis. Curve 992 plots concentration at zero minutes, curve 994 plots concentration at 30 minutes, curves 995, 996, 997 and 998 plot concentrations at 60, 90, 60 and 180 minutes respectively.

Another useful example may advantageously comprise an LLSi system with an image volume of 34.5 mm3 (7.2 mm×4.8 mm and focal depth of 1 mm, and an optical resolution of ~5 µm) to image 34-3456 bacterial cells to detect sufficient number of bacterial cells at clinically relevant concentrations (e.g., $10^3$-$10^5$ CFU/mL for bacteria in UTI). The image volume is determined by light slab that illuminates the sample, and by the viewing size and focal depth of the optics. Because LLSi determines the morphology and size of a cell from the intensity changes, in certain embodiments high signal-to-noise ratio is beneficial. To minimize background light, 90-degree scattering angle geometry may advantageously be used. The signal (scattered light intensity) may be maximized by selecting appropriate laser power that does not affect the sample. A 90-mW laser was used in preliminary experiments without observation of any heating of the sample. This laser power corresponds to an intensity of 30 mW/mm$^2$, which is low compared to the typical illumination intensity of optical microscopy because of the large illumination area. An intensity-stabilized laser has been used to reduce laser intensity fluctuations. To capture the motion of the bacterial cells, the imaging acquisition speed must be sufficiently fast. However, fast imaging lowers the number of photos per pixel, thus increasing short noise. It is believed that using the above-described apparatus, 20 fps imaging speed can be achieved, which corresponds to ~100 nm diffusion distance for the Brownian motion.

Tracking Single Bacterial Cells

Although DL treats the LLSi video as an input without the need of extracting specific features, in certain embodiments the video must contain substantially all of the phenotypic features (e.g., essential phenotypic features). In certain embodiments, the phenotypic features may include one or more of growth, motion, and possibly morphology change. In certain embodiments, this requires that the video have sufficient signal-to-noise ratio and temporal resolution, which can be optimized using the strategies described above. In certain embodiments, to ensure that the LLSi video contains all the essential information for AST, different phenotypic features from the video may be studied. Growth is relatively easy to determine from the LLSi as one bright spot splits into two spots. Since LLSi's optical resolution is larger than the size of bacteria, to determine the size and morphology changes, the intensity of each individual bacterial cell vs. time is determined, and the autocorrelation of the intensity his studied. The preliminary data, some of which is set out above, show that the intensity of *E. coli* cells fluctuates over time, which is primarily due to the rotation of the elongated cells. The autocorrelation thus contains rotational relaxation time, which reflects the shape of the cell. The average intensity over a time period much longer than rotational relaxation time contains gradual size and morphology change of the cell, which also be tracked and analyzed. The position of the bacterial cells his tracked by fitting the intensity distribution of each bacterial cell (bright spot) with a two dimensional Gaussian and able to obtain nanometer tracking precision.[26]

The LLSi video described herein provides detailed growth, morphology and motion changes of individual bacterial cells, but providing the entire video as an input to the DL algorithm is computational prohibitive. To minimize the computational burden, the video may advantageously be compressed into a static image without losing information (e.g., essential information, in certain embodiments, on the growth, size (morphology) and motion changes. Time sequence images are overlaid into a static trace image, which reveals the two-dimensional trace of a moving bacterial cell. The traces of the individual bacterial cells in the static trace image contains beneficial information of antibiotic action on the bacteria, which provides a good input for DL as shown herein. When growth (division of a cell into two) occurs, a branch in the trace appears. The speed of the motion is reflected in the length of the trace, and intensity variation along the trace. When the bacterial cell increases in size, the average intensity along the trace increases according to the 6th power of the size in LLSi (light scattering).

Efficient Training of DL for Fast AST

In one useful hypothetical example, after compressing the LLSi videos, a DL model may use the convolutional neural network method. This task consists of two steps. The first step is to train the DL model to learn the hidden features from the trace images of bacteria that are inhibited or not by an antibiotic at a concentration. To generate a large data set for training, two sets of LLSi videos may be recorded. A first set without antibiotics, and a second set with a highly concentrated antibiotic to inhibit the bacteria.

In a preliminary test example, a training data set was generated for *E. coli* O157 consisting of about 6000 bacterial cell traces including 3000 inhibited by PMB (antibiotic), and 3000 controls. The training data set was fed into the DL model in an iterative way. Each iteration used 200 bacterial traces randomly selected from the 6000 traces to train and optimize the DL model. In one useful example, 200 iterations provided excellent accuracy, which took ~2 hours using an office computer equipped with Intel® Core™ i7-4790 CPU @3.60 GHz. The dependence of the accuracy on the size of the training data was found to determine the optimal training size to achieve accurate AST. For this task, a higher performance computer may be used (e.g., 44 nodes with Intel Xeon E5-2640 and ASU Supercomputing Facilities). Further, more experimental data may advantageously be generated for different bacterial strains and different antibiotics used for UTIs. The reliability of the training data set may be improved by using supporting techniques i.e., fluorescence viability test kits to help label the training data accurately.

After the DL model is trained, it can be tested with different strains and different antibiotics. For each bacterial strain, the concentration of each antibiotic can be systematically varied to generate an inhibition curve, which plots the number of viable (or non-viable) bacterial cells vs. antibiotic concentration. From the inhibition curve, the MIC value can be obtained, and compared with that obtained from traditional culture-based method. Although the training process may take hours, it is one-time only, and the testing process is much faster. For example, it took less than 5 minutes for 6000 bacterial traces using the office computer mentioned above.

Deep Learning Video Microscopy-Based Antimicrobial Susceptibility Testing (DLVM-AST)

Figure 7:
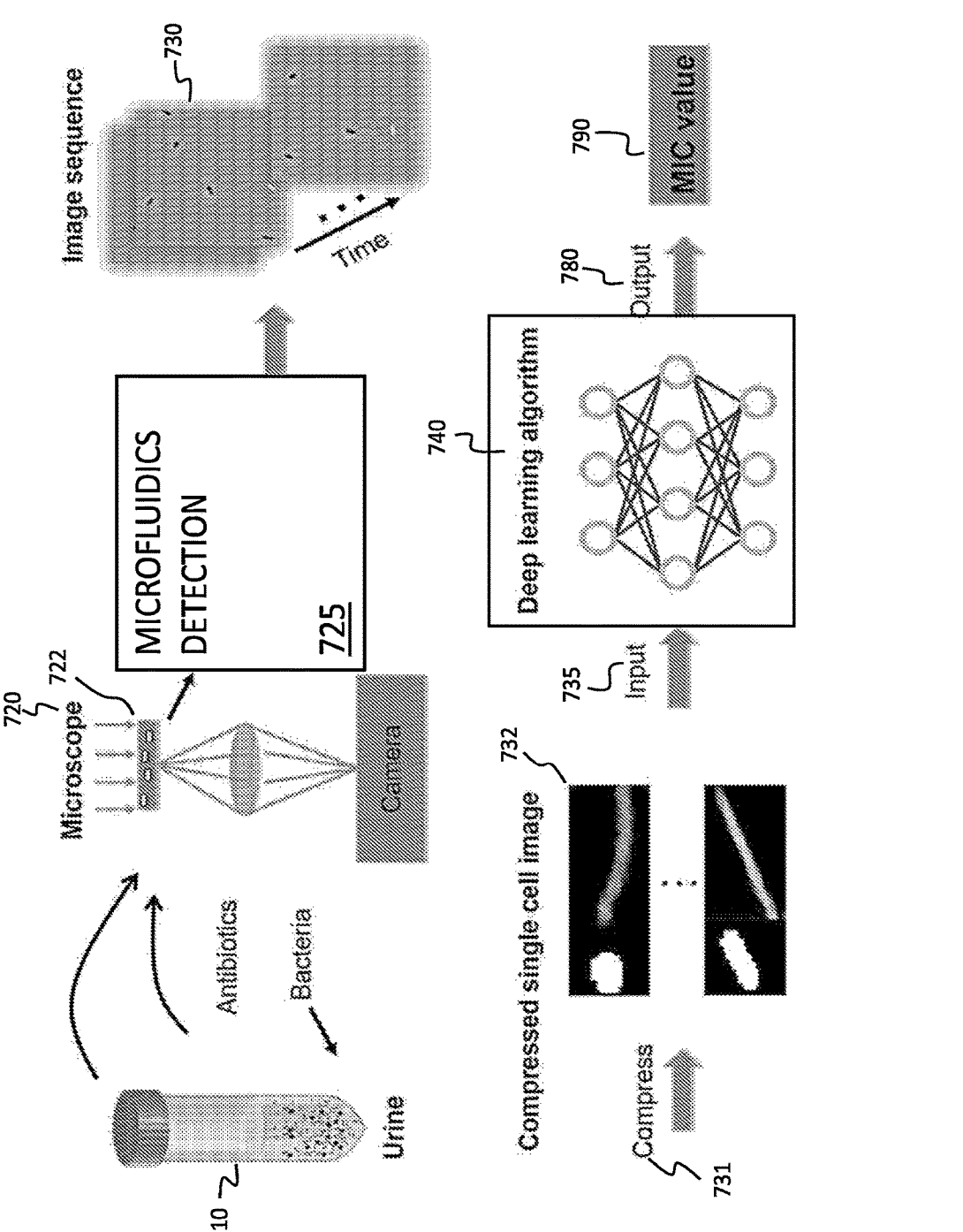
FIG. 7 schematically shows an example of a deep learning video microscopy-based antimicrobial susceptibility testing (DLVM-AST) method.

Referring now to FIG. 7, an example of a deep learning video microscopy-based antimicrobial susceptibility testing (DLVM-AST) method is schematically shown. The workflow of DLVM-AST consists of 1) acquiring an image sequence of single bacterial cells in a subject sample, as for example urine samples, with a phase contrast microscope before, during, and after exposure to each antibiotic at different concentrations, 2) compressing the image sequence into static images while preserving essential phenotypic features, 3) inputting data representing the static images into a DL model (e.g. pre-trained with thousands of images), and 4) obtaining antimicrobial susceptibility and MIC for the bacterial strain.

In one example, urine samples 710 were mixed with antibiotics at different concentrations and imaged with a microscope 720 in a microfluidic chip 722 without immobilization onto a sensor surface or in gels to simplify sample preparation. This also allowed the bacterial cells to move freely in urine solution (e.g., swimming and tumbling)[28, 29], thus capturing phenotypic features that are not trackable with immobilized bacterial cells. It was observed that the bacterial cells frequently moved in and out of the microscope view and focus. As a result, following each of them over time proved difficult with the conventional image processing method. DLVM-AST overcame this difficulty because it did not rely on tracking a specific feature of a bacterial cell. Videos, representing image sequences 730, of bacteria were recorded over time and compressed into static images 732 containing single cell features. A deep learning algorithm 740 was used to determine the minimum inhibitory concentration (MIC) value 790 from the sub-videos 780.

Figures 8A, 8B, 8C:
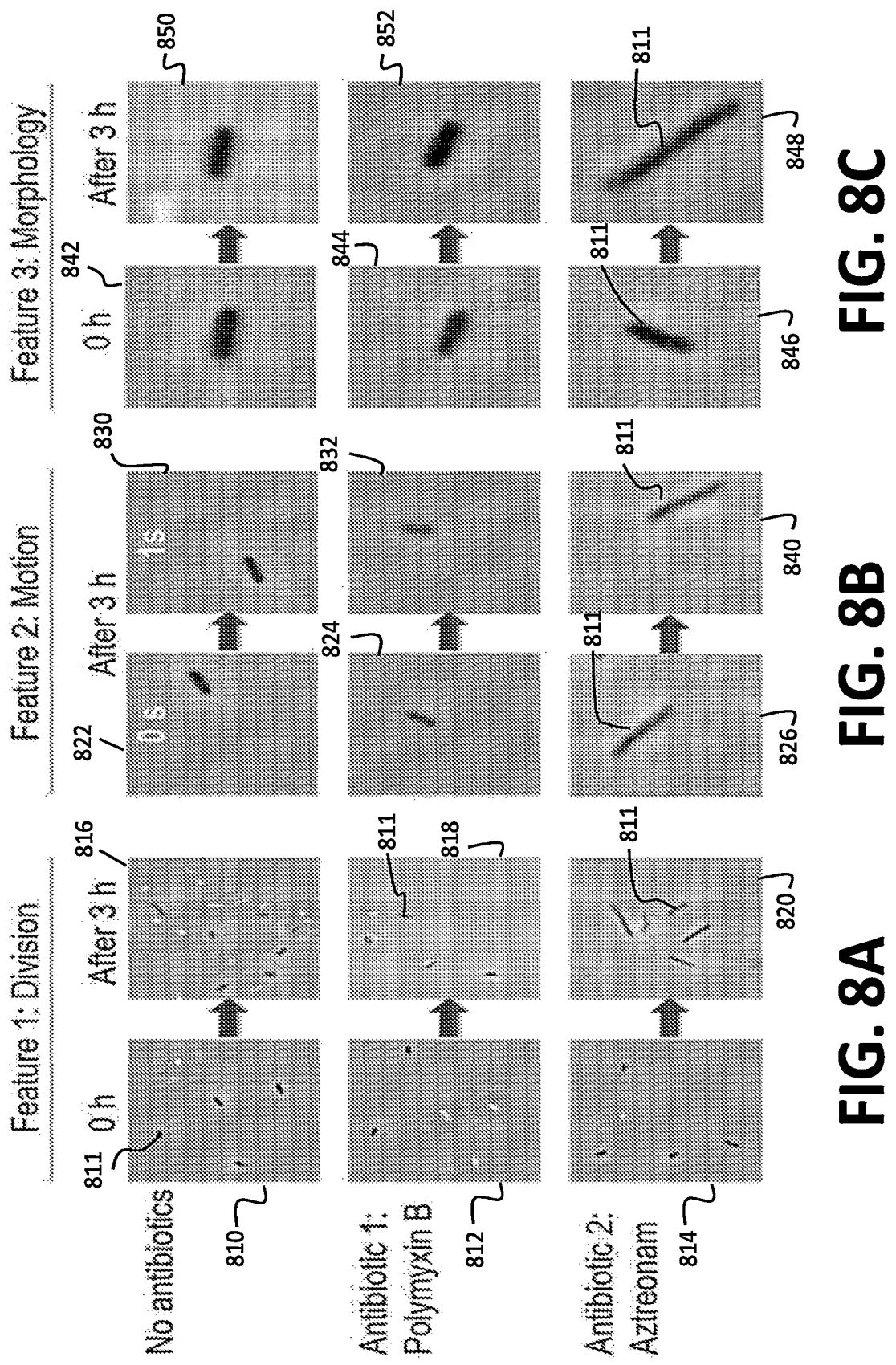
FIG. 8A-FIG. 8C show phenotypic features in the recorded bacteria videos in the presence and absence of antibiotics

Referring now simultaneously to FIG. 8A-FIG. 8C, phenotypic features in the recorded bacteria videos in the presence and absence of antibiotics are shown. Three features, division (feature 1, as shown in FIG. 8A), motion (feature 2, as shown in FIG. 8B), and morphology (feature 3, as shown in FIG. 8C) are displayed in snapshots of bacteria, generally indicated as reference number 811, collected from the recorded videos. Concentrations of PMB and aztreonam are 8 µg/mL and 0.5 µg/mL, respectively.

In principle, the raw bacterial videos could be used as inputs for a DL model, but the computational expense is impractical. In fact, few DL applications could use videos as input data directly even with high performance super-computers.30-32 To overcome this difficulty, a method to compress the raw videos into static images without losing key phenotypic features was developed as described further below. This approach imitates human vision, which preprocesses raw images in the vision system to reduce complexity before passing them to the brain. The key phenotypic features in the video include cell division, motion, and morphology. A bacterial cell grows and divides, so cell division is a useful phenotypic feature to indicate if the cell is killed or its growth is effectively inhibited by an antibiotic. Cell motion and morphology may also change when exposing the cell to antibiotics, thus serving as additional phenotypic features for AST. It was found that the motion and morphology changes of *E. coli* were different for different antibiotics. For example, while PMB decreased bacterial motion, aztreonam caused the bacterial cells to elongate. These observations underscore the value of tracking both the motion and morphology as phenotypic features in addition to cell division, particularly for slowly dividing bacterial strains.

Referring specifically to FIG. 8A, panels 810, 812 and 814 illustrate feature 1, division, at time T=0 hours. Panels 816, 818 and 820 illustrate feature 1, cell division, after 3 hours have elapsed. No antibiotics were used on the cells shown in panels 810, 816. A first antibiotic, Polymyxin B was used on the cells shown in panels 812, 818. A second antibiotic, Aztreonam was used on the cells shown in panels 814, 820.

Referring specifically to FIG. 8B, panels 822, 824 and 826 illustrate feature 2, motion, at time T=0 hours. Panels 816, 818 and 820 illustrate feature 2, motion, after 3 hours have elapsed. No antibiotics were used on the cells shown in panels 822, 830. A first antibiotic, Polymyxin B was used on the cells shown in panels 824, 832. A second antibiotic, Aztreonam was used on the cells shown in panels 826, 840.

Referring specifically to FIG. 8C, panels 842, 844 and 846 illustrate feature 3, morphology, at time T=0 hours. Panels 816, 818 and 820 illustrate feature 3, morphology, after 3 hours have elapsed. No antibiotics were used on the cells shown in panels 842, 850. A first antibiotic, Polymyxin B was used on the cells shown in panels 844, 852. A second antibiotic, Aztreonam was used on the cells shown in panels 846, 848.

Figure 9:
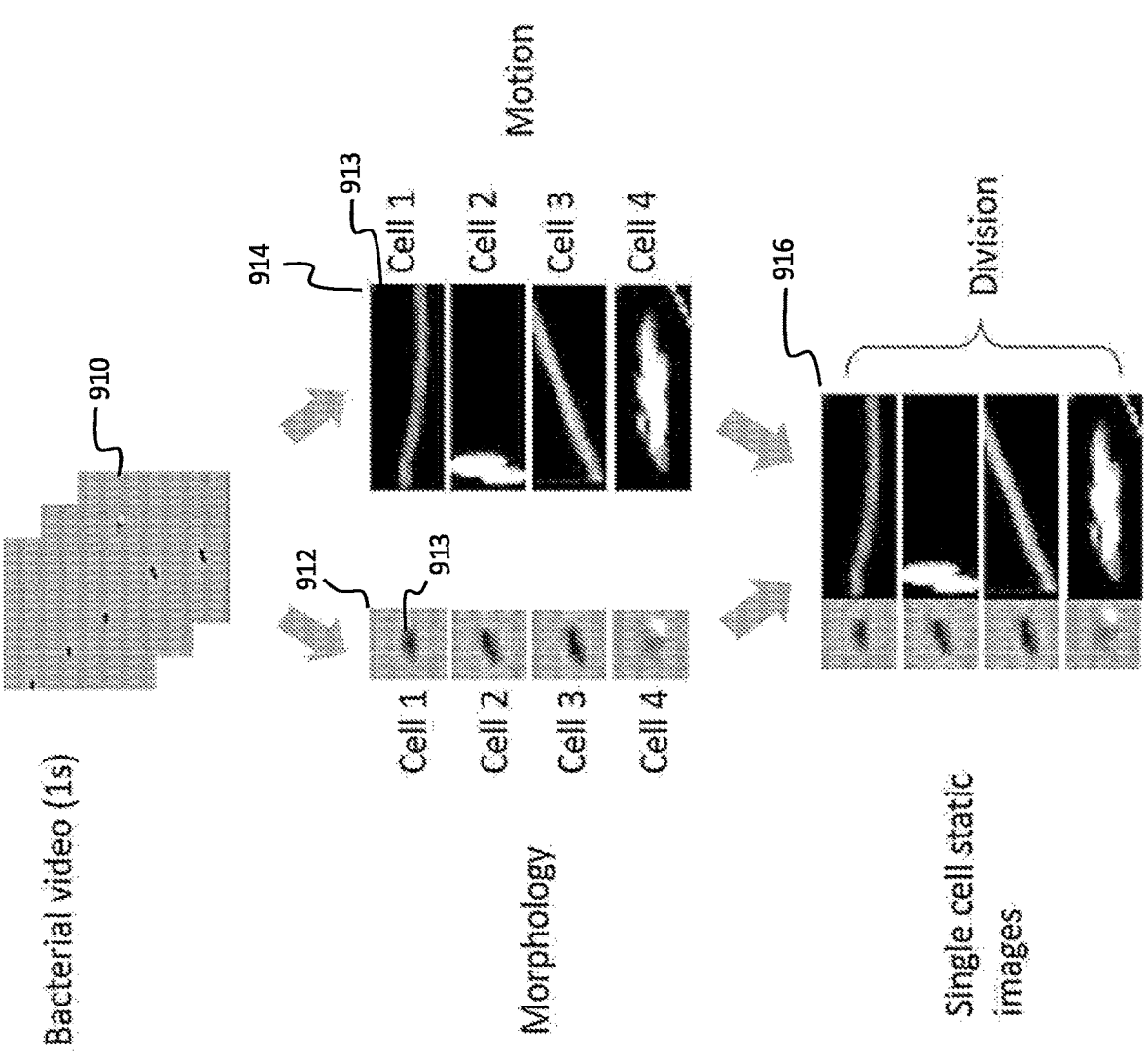
FIG. 9 shows an example of compression of a video of bacteria into single cell static images without losing key phenotypic features.

FIG. 9 shows an example of compression of a video of bacteria into single cell static images without losing key phenotypic features. The morphology feature was determined as snapshots of bacterial images, and the motion feature was determined as the bacterial dwelling time at each pixel. Morphology and motion features were merged into static images containing single cell features, and the number of cells was counted as the division feature.

The bacterial videos were compressed while preserving the essential phenotypic features described above using the strategy shown. Each video 910 (e. g. having a duration of 1 s) is compressed into two sets of static images 912, 914, capturing the morphology and motion of a single bacterial cell 913, respectively. The image containing the morphological feature 912 is a snapshot of the bacterial cell. In contrast, the image containing the bacterial movement 914 is the superposition of the binarized individual frames in the video, which represents the motion of the cell as a trace in the binary image. The cell division feature is present in both sets of the static images. The two sets of static images 912, 914 are merged into a single set of images 916 as the input data for the DL model. The model automatically learns and determines antimicrobial susceptibility from the input data at pixel level without specifically extracting high-level features. This strategy is different from the traditional cell imaging analysis, which defines and then quantifies each of the phenotypic features at single cell level, such as size, perimeter length, and speed.

Figures 10A, 10B, 10C:
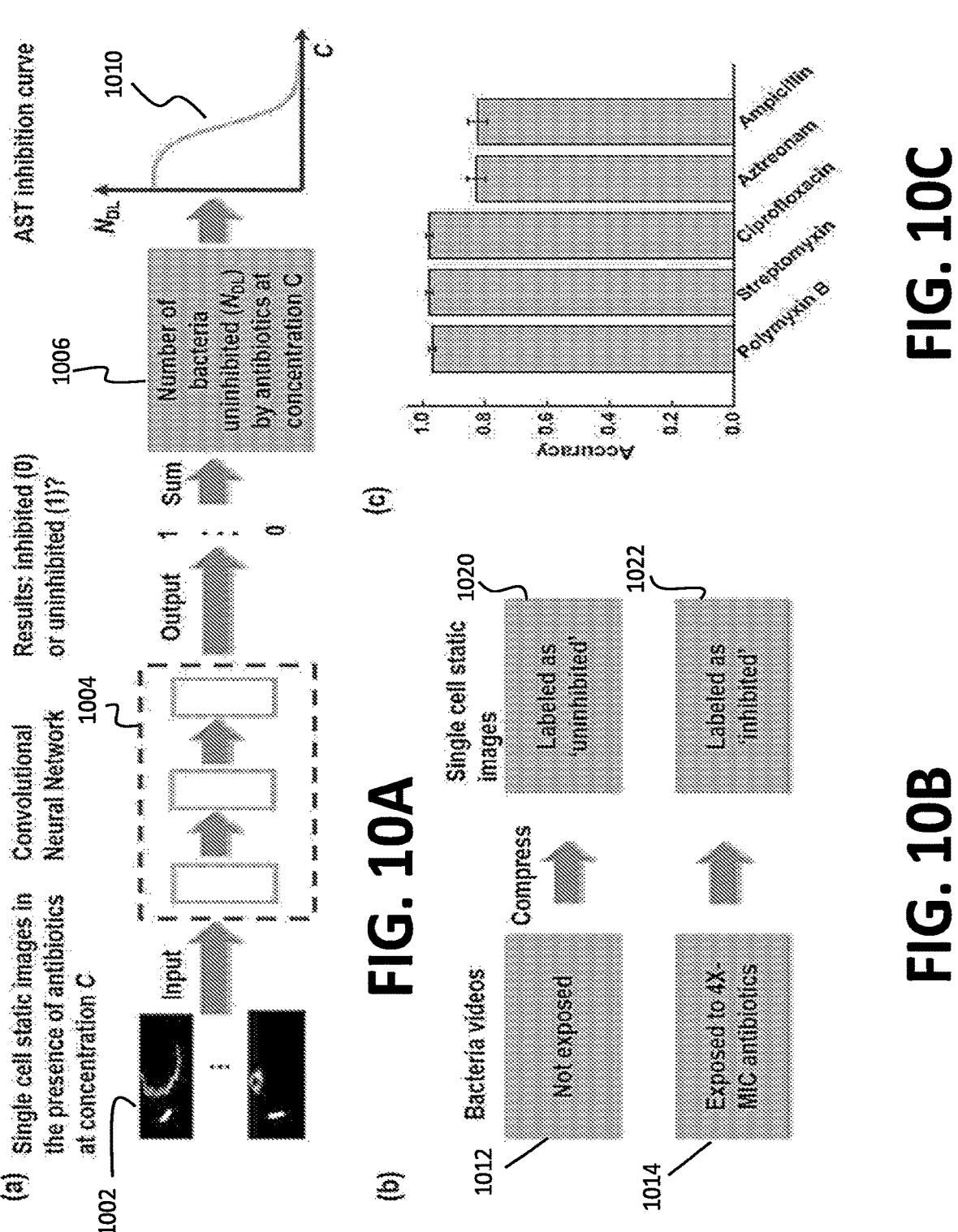
FIG. 10A schematically illustrates a deep learning (DL) workflow for determining MIC values.
FIG. 10B schematically illustrates preparation of a DL training dataset.
FIG. 10C graphically illustrates accuracy of a DL model in recognizing the effect of five antibiotics on each bacterial cell.

Referring now to FIG. 10A, a deep learning (DL) workflow for determining MIC values is schematically illustrated. Single cell static images 1002 of each bacterium spiked in urine were collected in the absence and presence of antibiotics at different concentrations and input into the pre-trained convolutional neural network model 1004. The DL model determines if each bacterium was inhibited or un-inhibited upon antibiotic exposure 1006 and automatically constructs an AST inhibition curve 1010. The DL algorithm uses a convolutional neural network model33, which includes two hidden convolutional layers, two subsampling layers, a fully connected layer, and an output layer. For each input image, the model produces an output of "1" if the cell is inhibited (or killed) by the antibiotic, and "0" if it is uninhibited. The model then determines the total number of uninhibited bacterial cells (NDL) over time for each antibiotic concentration (C) and produces inhibition curves (NDL vs. C) from which the MIC value is determined, describing the minimal concentration of an antibiotic that inhibits the bacterial strain.

Referring now to FIG. 10B, preparation of a DL training dataset is schematically illustrated. Prior to AST, the DL model was trained to learn to differentiate antibiotic effects on bacterial cells from the input data (images). A practical difficulty in many DL applications is the preparation of a large training dataset to train the model.34 This difficulty was overcome by recording two sets of videos 1012, 1014, each containing more than 100 bacterial cells. One video 1012 was for bacterial samples not exposed to antibiotics, and the second video 101 was for samples treated with concentrated antibiotics (4× higher than the MIC value) for 6 hours to ensure inhibition of all the bacterial cells. The bacterial cells in the former video were assumed to be and labeled as "uninhibited" 1020, and those in the latter as "inhibited" 1022 by the antibiotics. The videos were segmented into multiple sub-videos (1 s duration). The sub-videos were then compressed into single cell static images using the procedure described earlier and introduced into the DL model for training.

Referring now to FIG. 10C, accuracy of a DL model in recognizing the effect of five antibiotics on each bacterial cell is graphically illustrated. The DL model produces an output for each input image in the data, and the accuracy was determined as the percentage that DL output coincided with the original label in (b). For each data set, the error bar is the standard deviation of accuracy in 30 individual training runs. The accuracy of models for five antibiotics as shown. The training accuracies for the antibiotics are 97.5% for PMB, 98.5% for streptomycin, 98.0% for ciprofloxacin, 82.7% for aztreonam, and 82.3% for ampicillin, respectively. The training for each antibiotic lasted about 15 minutes using an office desktop computer.

Figure 11A:
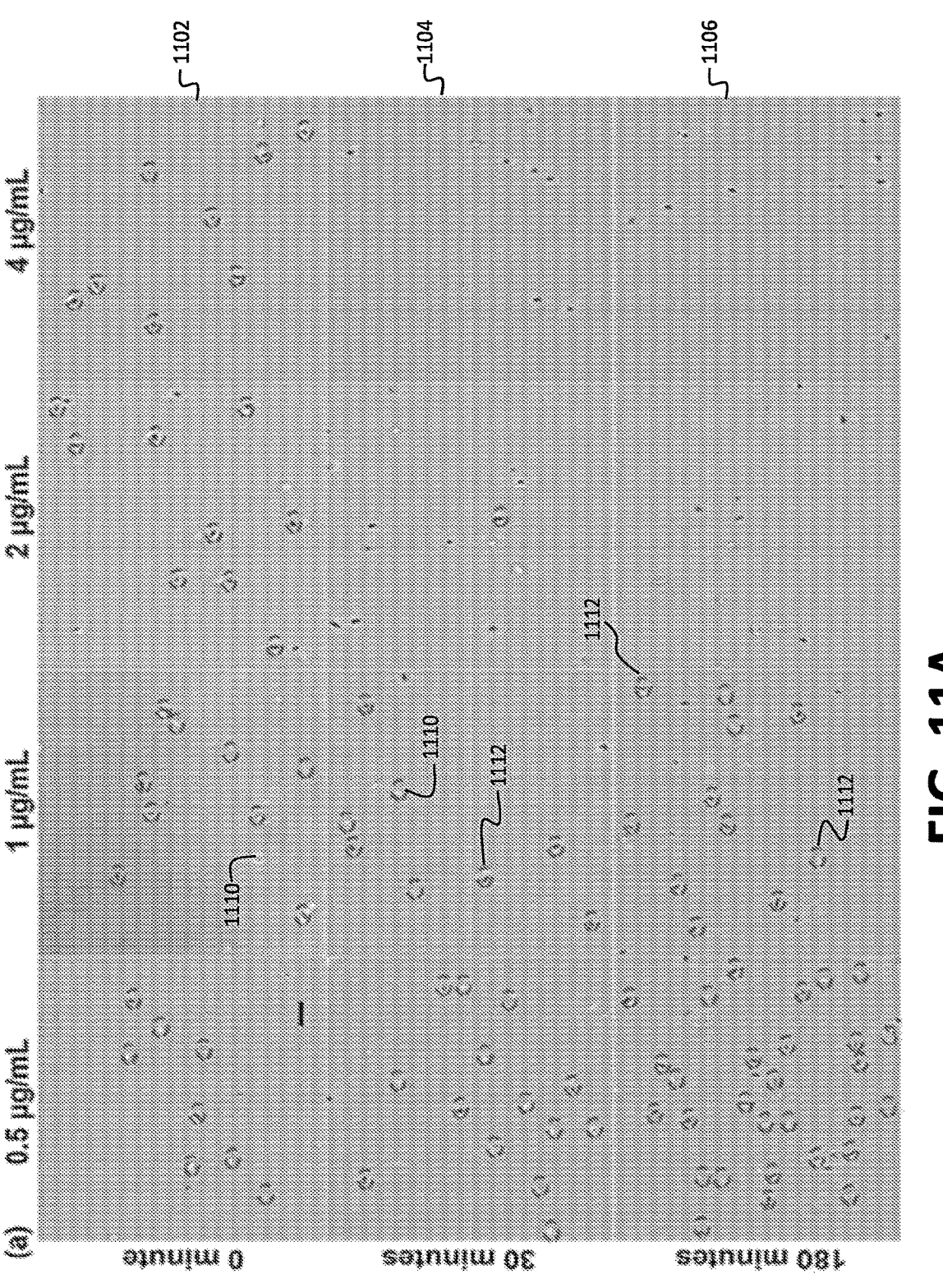
FIG. 11A shows AST results with PMB on *E. coli* as typical microscopic images recorded in the presence of PMB at different concentrations and after different treatment times.

FIG. 11A shows AST results with PMB on *E. coli* as typical microscopic images recorded in the presence of PMB at different concentrations and after different treatment times. Bacterial cells 1110 appear as dark and bright spots in the images, while those cells marked with dashed circles 1112 were recognized by the DL model to be phenotypically uninhibited upon exposure to PMB. After DL training, DLVM-AST was performed for *E. coli* against five different antibiotics and the results validated with the gold standard BMD method. 30 s-interval videos of bacterial cells were recorded in the presence of antibiotics at a given concentration every 30 minutes over 6 hours, and then these assays were repeated with different antibiotic concentrations. Panel sequences 1102, 1104 and 1106 respectively show typical snapshots of *E. coli* (bright or dark rods 1110) captured before and 30 and 180 minutes after exposing the sample to PMB at different concentrations, where dashed circles marked bacterial cells 1112 were determined by the DL model to be "uninhibited". The videos were then segmented into 30 sub-videos (e. g. 1 s duration) and each sub-video was compressed using the procedure described above, and the single cell static images were introduced into the pre-trained DL model to determine the number of uninhibited cells (NDL) in each sub-video.

Figure 11B:
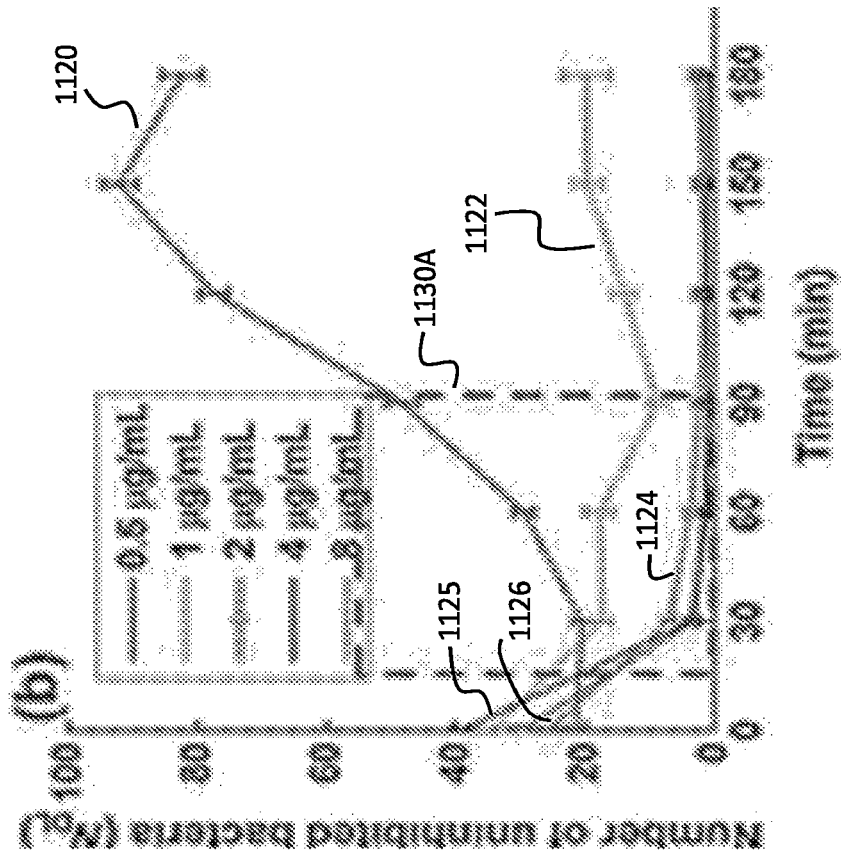
FIG. 11B shows an inhibition curve plotted as number of uninhibited bacteria determined by the DL versus treatment time at different PMB concentrations.

Referring now to FIG. 11B, an inhibition curve (NDL (mean±std) vs. time) was then plotted for each PMB concentrations as number of uninhibited bacteria determined by the DL versus treatment time at different PMB concentrations. Curves 1120, 1122, 1124, 1125 and 1126 respectively plot the number of uninhibited bacteria versus time at concentrations of 0.5, 1, 2, 4, and 8 µg/mL. If MIC is defined as the antibiotic concentration at which 90% of the bacterial cells are inhibited, then the MIC for PMB obtained 30 minutes after antibiotic treatment is 2 µg/mL. This MIC agrees with that obtained with the gold standard BMD method performed overnight (see Table 1).

TABLE 1

The MIC values (µg/mL) and assay time (h) determined
by the three methods for all five antibiotics,
with each test performed in triplicate.

| Antibiotics | MIC/time (µg/mL)/h DLVM-AST | MIC/time (µg/mL)/h AST Without DL* | MIC/time (µg/mL)/h BMD** |
|---|---|---|---|
| Polymyxin B | 2/0.5 | 1-2/3 | 2/16 |
| Streptomycin | 4/3 | 4/4 | 4/16 |
| Ciprofloxacin | 0.03/3 | 0.015-0.03/4-5 | 0.03/16 |
| Aztreonam | 0.12/1.5 | 0.12/3 | 0.12/16 |
| Ampicillin | 2/2.5-3 | 2/4 | 2/16 |

*AST without DL: AST determined by division feature only.
**BMD: Broth Macrodilution.

Figure 11C:
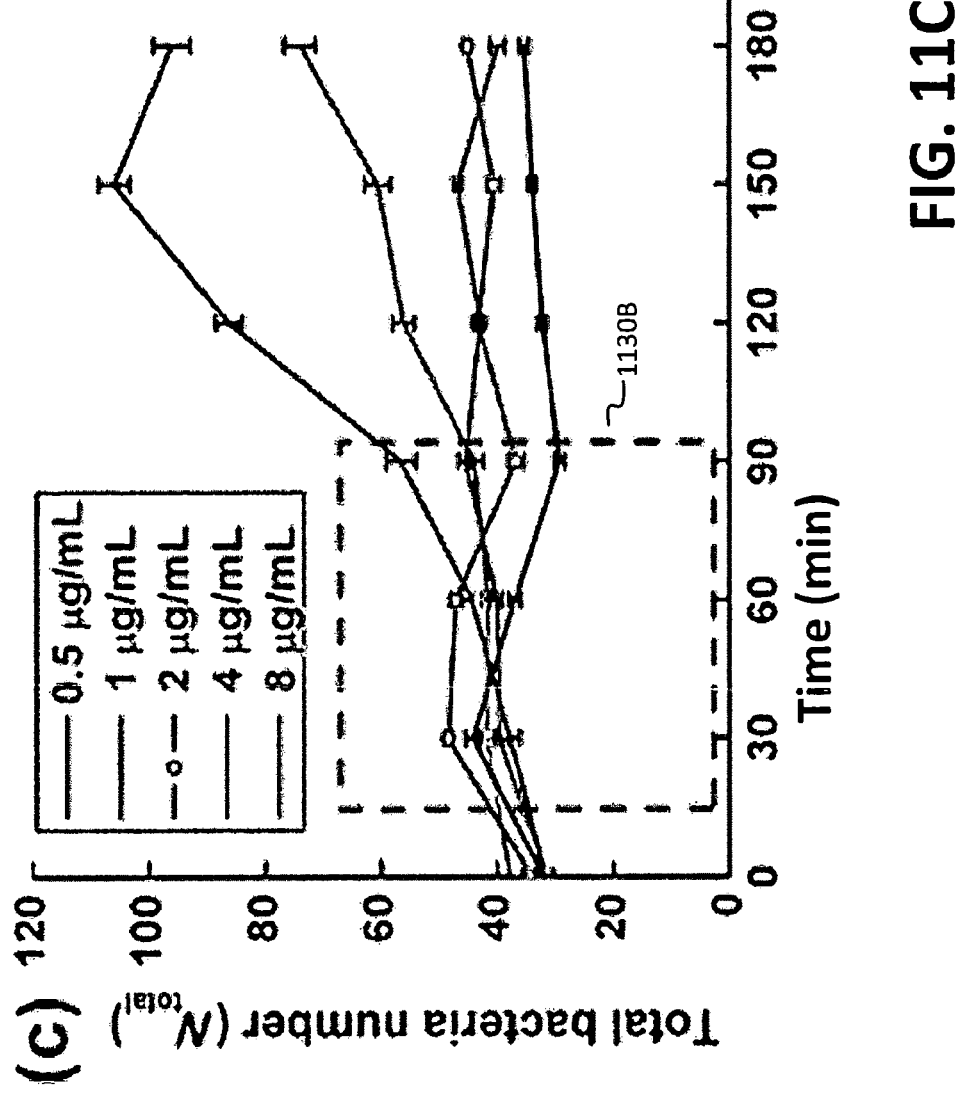
FIG. 11C shows an inhibition curve plotted as the total bacterial number determined by the division feature without DL versus treatment time at different PMB concentrations.
Figure 11D:
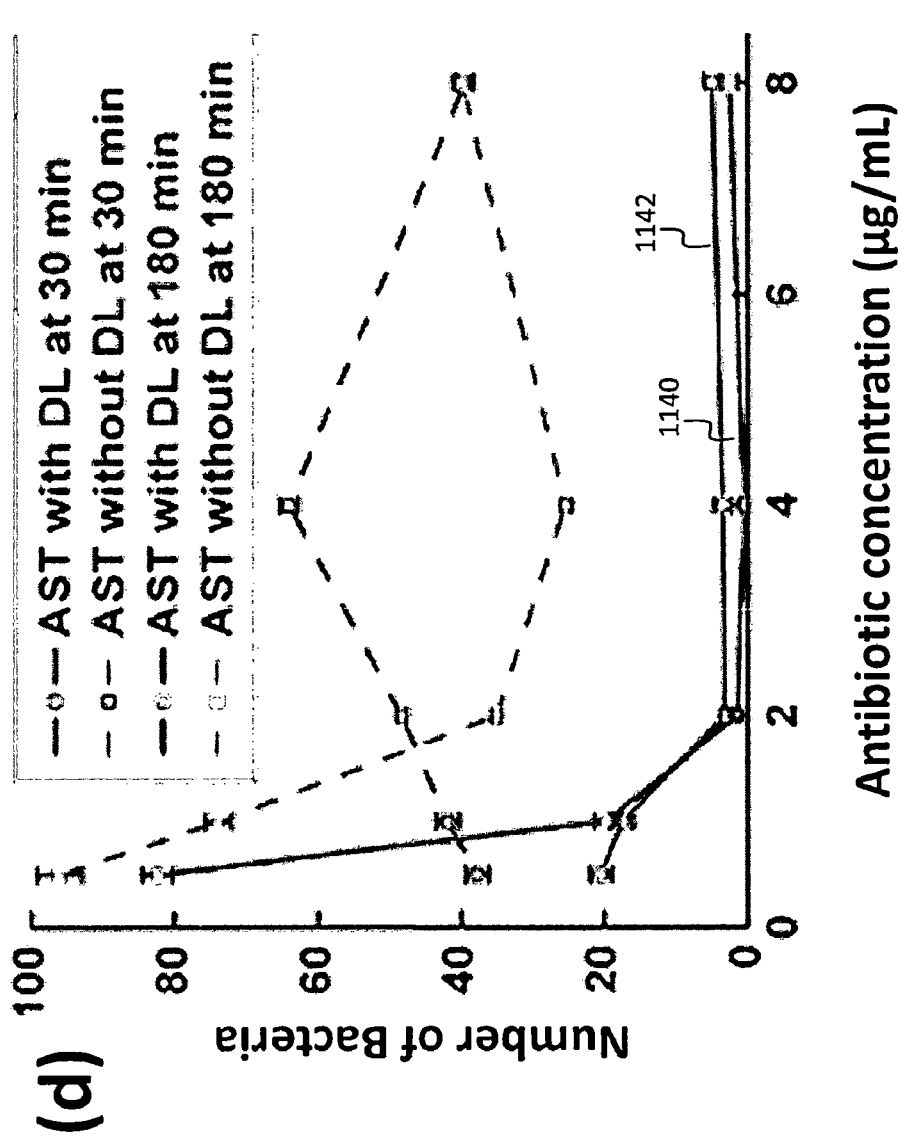
FIG. 11D shows a comparison of inhibition curves of DLVM-AST and AST without DL after PMB exposure for 30 and 180 minutes.

To further validate the DLVM-AST method, we counted the total number of bacteria cells ($N_{total}$) from the videos (as shown in FIG. 9), and plotted $N_{total}$ (mean±std) vs. time for PMB at various concentrations (as shown in FIG. 11C). The plots show that $N_{total}$ increased over time (reflecting the growth and division of the bacterial cells) at low concentration PMB but changed little over time (indicating effective inhibition) at concentrated PMB. We obtained inhibition curves for PMB by plotting $N_{total}$ vs. antibiotic concentration (as shown in FIG. 11D), from which a MIC value of ˜2 µg/mL (curve 1140) at 180 minutes was found. This MIC value is consistent with that obtained by DLVM-AST at 30 minutes, curve 1142. However, the inhibition curve obtained with this cell counting method at 30 minutes does not show any obvious change in the number of bacterial cells, demonstrating superior performance with DLVM-AST.

Using a similar procedure, DLVM-AST was performed with streptomycin, ciprofloxacin, aztreonam, and ampicillin on *E. coli*, each test repeated three times on different days. The results are summarized in Table 1, showing that the MIC values obtained by DLVM-AST are consistent with those by the gold standard BMD method for all the antibiotics. The assay time of the present DLVM-AST method varies with the antibiotics, due to different antimicrobial mechanisms for these antibiotics. Despite the variability in the assay time, DLVM-AST shortens the assay time to less than 3 hours for all the antibiotics, compared to the overnight assay for the BMD method.

An important reason that the present DLVM-AST method is faster than the BMD and traditional microscopy-based AST methods based on cell counting without DL is its inclusion of multiple phenotypic features and analysis of the features at the pixel-level. Additional phenotypic features could also be included in the cell counting method based on the traditional image processing and classification techniques without using DL.14 However, defining and quantifying various phenotypic features, such as swimming, tumbling, filament formation, swelling and morphology changes, are difficult. DLVM-AST offers a universal solution to learn one or a combination of features from the videos without specifically defining and quantifying each specific feature.

Referring now jointly to FIG. 11B and FIG. 11C, note the obvious pattern difference between FIG. 11B and FIG. 11C in the dashed rectangular regions 1130A and 1130B. FIG. 11D shows a comparison of inhibition curves of DLVM-AST and AST without DL after PMB exposure for 30 and 180 minutes. The bar for each plot FIG. 11B-FIG. 11D is 5 µm.

Once trained, the DLVM-AST model can be used anytime afterwards and quickly (˜5 minutes) predict MIC values from the videos. In fact, a pre-trained DL model was applied to perform AST 4 months after acquiring the results above to produce data shown in FIG. 11B-FIG. 11D and Table 1.

Figure 12:
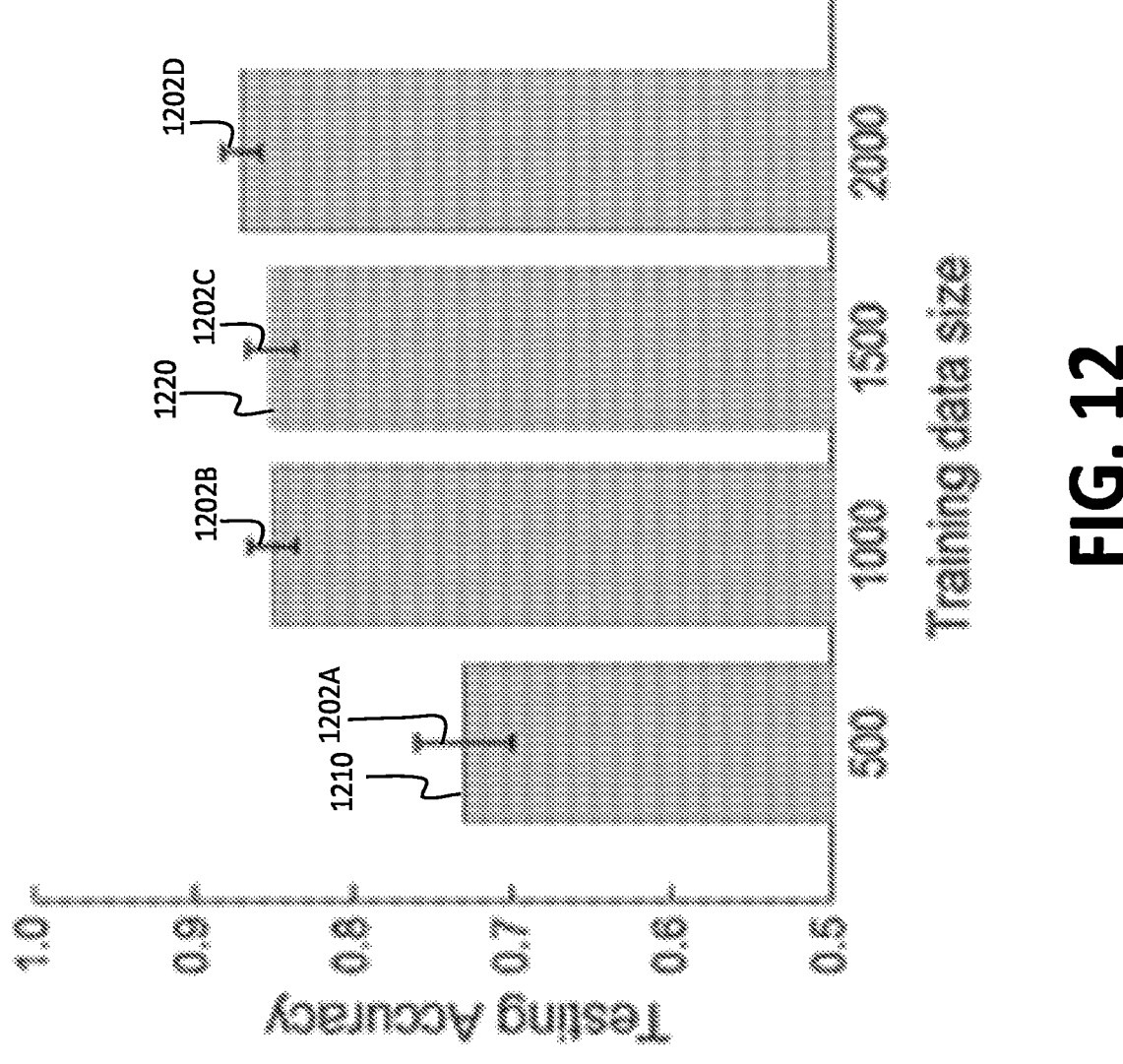
FIG. 12 shows an example of the self-learning capability of the deep learning model (DL).

Referring now to FIG. 12, an example of the self-learning capability of the deep learning model (DL) is shown. One example of the DL model was trained with increasing training data size, and testing dataset was obtained from the next AST assay. The accuracy of the DL model improves with the increasing training data size for AST with ampicillin. Error bars 1202A-1202D represent standard deviation of accuracy in 30 individual training runs. Another unique advantage of the DLVM-AST method is its self-learning capability, which adds each additional test to the training dataset to improve the accuracy for the next AST experiment. For example, if the DL model is trained with 500 single cell images, bar 1210, the results show an accuracy of 73%±3.1% for ampicillin. This accuracy increases to 87%±1.2% after testing additional 1500 datasets as indicated by bar 1220. This self-learning or improving capability is particularly attractive if the DLVM-AST method is widely adopted and vast amounts of test data become available to train and improve the DL model. While the examples described herein represent present work that focuses on videos, it will be understood that the DL model is not limited to phenotypic features captured in the videos, and could be expanded to include biochemical features, such as adenosine triphosphate (ATP) consumption, proteins and nucleic acids[9, 20, 23], to further improve its specificity and sensitivity.

Methods

Having fully described the methods, apparatus and systems employed in carrying out the invention, particular methods, preparations and techniques used in the examples herein will now be described to promote a better understanding of the invention.

Materials. Unfiltered human urine samples (Lot #: BRH1041997) and *E. coli* (ATCC 43888; Biosafety Level 1 organism that does not produce either Shiga-like I or II toxins and lacks the genes for these toxins) were purchased from Bioreclamation IVT Co. and Fisher Scientific, respectively. Antibiotics, including polymyxin B (PMB), ampicillin, streptomycin, ciprofloxacin, and aztreonam, and all other reagents were purchased from Sigma-Aldrich. The antibiotic powders were stored in dark at –2-8° C.

Antibiotic preparations. Stock solutions of PMB, ampicillin, and streptomycin at concentrations of 200 µg/mL were prepared by directly dissolving the antibiotics in ultrapure water. Ciprofloxacin and aztreonam were first dissolved in 0.1 M HCl (1:60, m/V) and dimethylformamide:methanol solution (1:1, V/V), respectively, and then diluted in ultrapure water to obtain stock concentrations of 200 µg/mL. These antibiotic stock solutions were stored in dark at –80° C. Before AST, the antibiotic stock solutions were thawed to room temperature and diluted in ultrapure water to various concentrations for AST, following guidelines recommended by the Clinical and Laboratory Standards Institute (CLSI)[35].

Growth and preparation of *E. coli*. Frozen *E. coli* strains were thawed, and 50 µL of which were cultured in 5 mL of Luria-Bertani (LB) medium (Per liter: 10 g peptone 140, 5 g yeast extract, and 5 g sodium chloride) at 37° C. and 150 rpm for 16 hours. Saturated cultures in the volume of 20 µL were diluted into 5 mL of fresh LB medium, and growth continued at 37° C. with 150 rpm for 1 hour to attain a logarithmic phase of growth. Bacterial cells were collected by centrifugation at 450 g for 5 min and suspended in urine to a concentration of $2 \times 10^7$ cells/mL[36]. This concentration was determined by measuring the extinction coefficients for *E. coli* from the Optical Density (OD600) reading taken with a spectrophototometer (NanoDrop™ 2000/2000c Spectro-photometers, Thermo Scientific). The calibration factor for bacterial cell cultures estimation was $8\times10^8$ cells/mL per OD600 unit. Before use, the bacteria-spiked urine samples were filtered using a 5 μm syringe filter (EMD Millipore) to remove large particles.

Fabrication and structure of the microfluidic chip. A microfluidic chip with a channel volume less than 100 nL was used to generate a stable microenvironment for the bacterial cells. The microfluidic chips were fabricated by multilayer soft lithography,[37-39] including pneumatic control and fluidic layers made of PDMS (RTV 615, the ratio of A/B is 5:1) and PDMS (RTV 615, the ratio of A/B is 10:1, Momentive Specialty Chemicals), respectively. The fluidic layer included a detection channel (0.5 cm long, 200 μm wide and 25 μm high) and inlet and outlet channels. The control and fluidic layers were aligned by thermopolymer-ization reaction and bonded on a glass slide with oxygen plasma. The mold of the control layer was made of negative photoresist (SU8-2025, Microchem), and the mold of the fluidic layer was made from a positive photoresist (AZ-50XT, AZ Electronic Materials USA Corp.). The microflu-idic chip has six parallel detection channels, which allowed AST detection with different concentration of antibiotics simultaneously. The fluids were kept inside the detection channel by closing the valves during video recording.

AST with video microscopy. The microfluidic chip was placed on an inverted microscope (Olympus IX-81) with a 40× phase contrast objective lens and imaged with a CCD camera (Pike-032B, Allied Vision Technologies, Newbury-port, Mass.). A 200-μL bacterial suspension ($2\times10^7$ cells/mL) was mixed with an equal volume of antibiotic solution for each antibiotic concentration or an equal volume of water as a control experiment. These mixed solutions were injected into different microfluidic channels simultaneously. After the microfluidic channels were fulfilled with these mixed solutions, two microfluidic valves of each detection channel were closed simultaneously to generate a stable microenvironment. Videos of the bacterial cells were recorded at 100 frames per second (fps) immediately (0 min) and after every 30 min. Each video lasted for 30 seconds. The raw images were batch-converted to 16-bit tiff format using a Matlab program and pre-processed to minimize background artifacts before being processed with the DL model. To include enough cells for reliable results, we integrated bacterial cells from three videos recorded from different experiments. Each experiment was repeated inde-pendently for three times.

Deep learning. The DL model was implemented with the TensorFlow™, an open-source software library for Machine Intelligence.[40] The training dataset included 1000 static single cell images, with 500 "inhibited", and 500 "uninhib-ited" (control) cells for each antibiotic tested. Each model was trained iteratively for 1000 iterations. In each iteration, 50 static images were randomly selected from the training dataset and input into the model. We examined the accuracy of the trained model using 300 static images (150 labeled "inhibited" and 150 labeled "uninhibited") upon exposure to each antibiotic. All the computations were performed with a desktop computer (Intel® Core™ i7-47PU @3.60 GHz).

AST with broth macrodilution (BMD) method. For com-parison, AST was also performed by the BMD method (CLSI gold standard[35]). The adjusted inoculum E. coli suspension is diluted in Cation-adjusted Mueller Hinton Broth (CAMHB, Sigma-Aldrich) and the concentration of E. coli cell cultures are adjusted to $1\times10^6$ cells/mL based on UV-Vis spectrophotometer (NanoDrop 2000, Thermo Fisher) readings at OD600. Within 15 minutes after the inoculum has been prepared, 1 mL of the adjusted inoculum is added to tubes containing 1 mL of antibiotics in two-fold dilution series or only broth (control group) and mix. This results in a 1:2 dilution of each antibiotics and inoculum concentration. After inoculation, each tube contains approxi-mately $5\times10^5$ cells/mL. After incubation at 37° C. for 16 hours, the MIC values can be read as the lowest concentra-tion without visible growth. This test was performed in triplicate.

Certain exemplary embodiments of the invention have been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without depart-ing from the true spirit and scope of the present invention.

REFERENCES

The teachings of the following publications are incorpo-rated herein in their entirety by reference.

1. Hancock, R. E. The end of an era? Nature Reviews Drug Discovery 6, 28-28 (2007).
2. Neu, H. C. The crisis in antibiotic resistance. Science 257, 1064-1074 (1992).
3. Rossolini, G. M., Arena, F., Pecile, P. & Pollini, S. Update on the antibiotic resistance crisis. Current Opinion in Pharmacology 18, 56-60 (2014).
4. O'Neill, J. Tackling drug-resistant infections globally: final report and recommendations. The review on antimi-crobial resistance (2016).
5. Dalgaard, P., Ross, T., Kamperman, L., Neumeyer, K. & McMeekin, T. A. Estimation of bacterial growth rates from turbidimetric and viable count data. International journal of food microbiology 23, 391-404 (1994).
6. Reller, L. B., Weinstein, M., Jorgensen, J. H. & Ferraro, M. J. Antimicrobial susceptibility testing: a review of general principles and contemporary practices. Clinical infectious diseases 49, 1749-1755 (2009).
7. Wiegand, I., Hilpert, K. & Hancock, R. E. Agar and broth dilution methods to determine the minimal inhibitory concentration (MIC) of antimicrobial substances. Nature protocols 3, 163-175 (2008).
8. O'Neill, J. Rapid diagnostics: stopping unnecessary use of antibiotics. Review on Antimicrobial Resistance (2015).
9. Davenport, M. et al. New and developing diagnostic technologies for urinary tract infections. Nat Rev Urol 14, 296-310 (2017).
10. Bergeron, M. G. & Ouellette, M. Preventing antibiotic resistance through rapid genotypic identification of bac-teria and of their antibiotic resistance genes in the clinical microbiology laboratory. Journal of clinical microbiology 36, 2169-2172 (1998).
11. Dutka-Malen, S., Evers, S. & Courvalin, P. Detection of glycopeptide resistance genotypes and identification to the species level of clinically relevant enterococci by PCR. Journal of clinical microbiology 33, 24-27 (1995).
12. Palmer, A. C. & Kishony, R. Understanding, predicting and manipulating the genotypic evolution of antibiotic resistance. Nature Reviews Genetics 14, 243-248 (2013).

13. Choi, J. et al. Direct, rapid antimicrobial susceptibility test from positive blood cultures based on microscopic imaging analysis. Scientific Reports 7, 1148 (2017).

14. Choi, J. et al. A rapid antimicrobial susceptibility test based on single-cell morphological analysis. Science translational medicine 6, 267ra174-267ra174 (2014).

15. Longo, G. et al. Rapid detection of bacterial resistance to antibiotics using AFM cantilevers as nanomechanical sensors. Nature nanotechnology 8, 522-526 (2013).

16. Lissandrello, C. et al. Nanomechanical motion of Escherichia coli adhered to a surface. Applied physics letters 105, 113701 (2014).

17. Syal, K. et al. Antimicrobial susceptibility test with plasmonic imaging and tracking of single bacterial motions on nanometer scale. ACS nano 10, 845-852 (2015).

18. Kinnunen, P. et al. Monitoring the growth and drug susceptibility of individual bacteria using asynchronous magnetic bead rotation sensors. Biosensors and Bioelectronics 26, 2751-2755 (2011).

19. Sinn, I. et al. Asynchronous magnetic bead rotation microviscometer for rapid, sensitive, and label-free studies of bacterial growth and drug sensitivity. Analytical chemistry 84, 5250-5256 (2012).

20. Liu, T., Lu, Y., Gau, V., Liao, J. C. & Wong, P. K. Rapid Antimicrobial Susceptibility Testing with Electrokinetics Enhanced Biosensors for Diagnosis of Acute Bacterial Infections. Annals of Biomedical Engineering 42, 2314-2321 (2014).

21. Mann, T. S. & Mikkelsen, S. R. Antibiotic susceptibility testing at a screen-printed carbon electrode array. Analytical chemistry 80, 843-848 (2008).

22. Ertl, P., Robello, E., Battaglini, F. & Mikkelsen, S. R. Rapid Antibiotic Susceptibility Testing via Electrochemical Measurement of Ferricyanide Reduction by Escherichia coli and Clostridium sporogenes. Analytical chemistry 72, 4957-4964 (2000).

23. Altobelli, E. et al. Integrated Biosensor Assay for Rapid Uropathogen Identification and Phenotypic Antimicrobial Susceptibility Testing. European Urology Focus (2016).

24. Baltekin, Ö., Boucharin, A., Tano, E., Andersson, D. I. & Elf, J. Antibiotic susceptibility testing in less than 30 min using direct single-cell imaging. Proceedings of the National Academy of Sciences 114, 9170-9175 (2017).

25. Frymier, P. D., Ford, R. M., Berg, H. C. & Cummings, P. T. Three-dimensional tracking of motile bacteria near a solid planar surface. Proceedings of the National Academy of Sciences 92, 6195-6199 (1995).

26. Bauer Valen, D. A. et al. Deep Learning Automates the Quantitative Analysis of Individual Cells in Live-Cell Imaging Experiments. PLOS Computational Biology 12, e1005177 (2016).

27. Chen, C. L. et al. Deep Learning in Label-free Cell Classification. Scientific Reports 6, 21471 (2016).

28. Lauga, E., DiLuzio, W. R., Whitesides, G. M. & Stone, H. A. Swimming in circles: motion of bacteria near solid boundaries. Biophysical journal 90, 400-412 (2006).

29. Sokolov, A. & Aranson, I. S. Physical properties of collective motion in suspensions of bacteria. Physical review letters 109, 248109 (2012).

30. Yue-Hei Ng, J. et al. in Proceedings of the IEEE conference on computer vision and pattern recognition 4694-4702 (2015).

31. Tran, D., Bourdev, L., Fergus, R., Torresani, L. & Paluri, M. in Proceedings of the IEEE International Conference on Computer Vision 4489-4497 (2015).

32. Simonyan, K. & Zisserman, A. in Advances in neural information processing systems 568-576 (2014).

33. Krizhevsky, A., Sutskever, I. & Hinton, G. E. in Advances in neural information processing systems 1097-1105 (2012).

34. Chen, X.-W. & Lin, X. Big data deep learning: challenges and perspectives. IEEE Access 2, 514-525 (2014).

35. Jean B., P. et al. Methods for Dilution Antimicrobial Susceptibility Tests for Bacteria That Grow Aerobically; Approved Standard-Tenth Edition. (2015).

36. Ying, S.-Y. Generation of cDNA Libraries. Methods in Molecular Biology 221 (2003).

37. Lee, C.-C. et al. Multistep Synthesis of a Radiolabeled Imaging Probe Using Integrated Microfluidics. Science 310, 1793 (2005).

38. Jing, W. et al. Microfluidic platform for direct capture and analysis of airborne Mycobacterium tuberculosis. Analytical chemistry 86, 5815-5821 (2014).

39. Jing, W. et al. Microfluidic device for efficient airborne bacteria capture and enrichment. Analytical chemistry 85, 5255-5262 (2013).

40. Internet URL tensorflow.org/get_started/mnist/pros.

The invention claimed is:

1. A method for deep learning video microscopy-based antimicrobial susceptibility testing (DLVM-AST) of a bacterial strain in a sample including non-immobilized bacterial cells and an antibiotic, the method comprising:

acquiring an image sequence of individual bacterial cells of the bacterial strain in a subject sample with a phase contrast microscope before, during, and after exposure to each antibiotic at different concentrations, wherein the acquiring of the image sequence comprises capturing one or more phenotypic features including a motion feature of the non-immobilized bacterial cells in the image sequence, wherein superposition of multiple images of the image sequence yields a trace representing the motion feature;

compressing the image sequence into one or more trace images static images while preserving essential phenotypic features, wherein the one or more trace images are generated by superposition of multiple images of the image sequence, wherein the one or more trace images represent the motion feature;

inputting data representing the static images into a pretrained deep learning (DL) model which generates output data; and determining antimicrobial susceptibility for the bacterial strain from the output data.

2. The method of claim 1 further comprising obtaining a minimum inhibitory concentration (MIC) value for the bacterial strain.

3. The method of claim 1 wherein the subject sample is a urine sample from a human patient.

4. The method of claim 1 wherein said capturing of one or more phenotypic features further comprises capturing one or more of a division feature and a morphological feature of the non-immobilized bacterial cells in the image sequence.

5. The method of claim 1 wherein the antibiotic is selected from the group consisting of Polymyxin B, streptomycin, ciprofloxacin, aztreonam, ampicillin, and combinations thereof.

* * * * *